United States Patent
Thatava et al.

(10) Patent No.: US 9,932,561 B2
(45) Date of Patent: Apr. 3, 2018

(54) DIFFERENTIATING INDUCED PLURIPOTENT STEM CELLS INTO GLUCOSE-RESPONSIVE, INSULIN-SECRETING PROGENY

(71) Applicant: Mayo Foundation for Medical Education and Research, Rochester, MN (US)

(72) Inventors: Tayaramma Thatava, Blue Ash, OH (US); Andre Terzic, Rochester, MN (US); Yogish C. Kudva, Rochester, MN (US); Yasuhiro Ikeda, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/340,161

(22) Filed: Jul. 24, 2014

(65) Prior Publication Data
US 2014/0356951 A1     Dec. 4, 2014

Related U.S. Application Data

(63) Continuation of application No. 13/553,064, filed on Jul. 19, 2012, now abandoned.

(60) Provisional application No. 61/510,818, filed on Jul. 22, 2011.

(51) Int. Cl.
*C12N 5/071* (2010.01)
*C12N 5/074* (2010.01)

(52) U.S. Cl.
CPC ......... *C12N 5/0696* (2013.01); *C12N 5/0677* (2013.01); *C12N 2500/46* (2013.01); *C12N 2500/90* (2013.01); *C12N 2500/98* (2013.01); *C12N 2500/99* (2013.01); *C12N 2501/119* (2013.01); *C12N 2501/16* (2013.01); *C12N 2501/335* (2013.01); *C12N 2501/385* (2013.01); *C12N 2501/41* (2013.01); *C12N 2501/415* (2013.01); *C12N 2501/60* (2013.01); *C12N 2501/603* (2013.01); *C12N 2501/605* (2013.01); *C12N 2501/606* (2013.01); *C12N 2501/608* (2013.01); *C12N 2501/727* (2013.01); *C12N 2506/45* (2013.01)

(58) Field of Classification Search
CPC ............ C12N 5/0696; C12N 2501/335; C12N 2501/727; C12N 2506/45
See application file for complete search history.

(56) References Cited

U.S. PATENT DOCUMENTS

| | | | |
|---|---|---|---|
| 8,048,999 | B2 | 11/2011 | Yamanaka et al. |
| 8,058,065 | B2 | 11/2011 | Yamanaka et al. |
| 8,129,187 | B2 | 3/2012 | Yamanaka et al. |
| 8,173,118 | B2 | 5/2012 | Terzic |
| 8,278,104 | B2 | 10/2012 | Yamanaka et al. |
| 2004/0241838 | A1 | 12/2004 | Johnson et al. |
| 2006/0084168 | A1 | 4/2006 | Thomson et al. |
| 2011/0200568 | A1 | 8/2011 | Ikeda et al. |
| 2012/0164731 | A1 | 6/2012 | Sakurai et al. |
| 2013/0029416 | A1 | 1/2013 | Thatava et al. |
| 2013/0273013 | A1 | 10/2013 | Revel et al. |
| 2017/0009210 | A1 | 1/2017 | Ikeda et al. |

FOREIGN PATENT DOCUMENTS

| | | |
|---|---|---|
| EP | 1 970 446 | 9/2008 |
| WO | WO 2007/054720 | 5/2007 |
| WO | WO 2007/069666 | 6/2007 |
| WO | WO 2008/066630 | 6/2008 |
| WO | WO 2008/088882 | 7/2008 |

OTHER PUBLICATIONS

Chen et al., "A small molecule that directs differentiation of human ESCs into the pancreatic lineage," *Nat Chem Biol.*, 5(4):258-265, Epub Mar. 15, 2009 with 20 pages Supplementary Material.

Zawalich and Zawalich, "Effects of glucose, exogenous insulin, and carbachol on C-peptide and insulin secretion from isolated perifused rat islets," *J Biol Chem.*, 277(29):26233-26237, Epub May 13, 2002.

Maehr et al., "Generation of pluripotent stem cells from patients with type 1 diabetes," *Proc. Natl. Acad. Sci. USA*, 106(37):15768-15773, Sep. 2009.

Tateishi et al., Generation of insulin-secreting islet-like clusters from human skin fibroblasts. *Journal of Biological Chemistry*, 283(4):31600-31607, Nov. 2008.

Thatava et al., "Indolactam V/GLP-1-mediated differentiation of human iPS cells into glucose-responsive insulin-secreting progeny," *Gene Therapy*, 18:283-293, print 2011, Epub Nov. 2010.

Feng et al., "Molecules that promote or enhance reprogramming of somatic cells to induced pluripotent stem cells," *Cell Stem Cell*, 4(4):301-312, Apr. 2009.

Jaenisch and Young, "Stem cells, the molecular circuitry of pluripotency and nuclear reprogramming," *Cell*, 132(4): 567-582, Feb. 22, 2008.

Nakagawa et al., "Generation of induced pluripotent stem cells without Myc from mouse and human fibroblasts," *Nat Biotechnol.*, 26(1):101-106, print Jan. 2008, Epub Nov. 2007.

Okita "Generation of mouse induced pluripotent stem cells without viral vectors," *Science*, 322(5903):949-953, Epub Oct. 2008.

Okita et al., "Generation of germline-competent induced pluripotent stem cells," *Nature*, 448: 313-317, Jul. 19, 2007.

Takahashi and Yamanaka, "Induction of pluripotent stem cells from mouse embryonic and adult fibroblast cultures by defined factors," *Cell*, 126(4):663-676, Epub Aug. 2006.

(Continued)

*Primary Examiner* — Kara Johnson
(74) *Attorney, Agent, or Firm* — Fish & Richardson P.C.

(57) ABSTRACT

This document provides methods and materials related to differentiating iPS cells into glucose-responsive, insulin-secreting progeny. For example, methods and material for using indolactam V (ILV) and glucagon like peptide-1 (GLP-1) to produce glucose-responsive, insulin-secreting progeny from iPS cells are provided.

9 Claims, 22 Drawing Sheets

(56) References Cited

OTHER PUBLICATIONS

Apolonia et al., "Stable gene transfer to muscle using non-integrating lentiviral vectors," *Mol. Ther.*, 15(11):1947-1954, print Nov. 2007, Epub Aug. 2007.

Behfar et al., "Cardiopoietic programming of embryonic stem cells for tumor-free heart repair," *J. Exp. Med.*, 204(2):405-420, Feb. 2007.

Behfar et al., "Stem cell differentiation requires a paracrine pathway in the heart," *FASEB J.*, 16(12):1558-1566, Oct. 2002.

Borowiak et al., "Small molecules efficiently direct endodermal differentiation of mouse and human embryonic stem cells," *Cell Stem Cell*, 4(4):348-358, Apr. 2009.

Buteau et al., "Glucagon-like peptide 1 induces pancreatic beta-cell proliferation via transactivation of the epidermal growth factor receptor," *Diabetes*, 52:124-132, Jan. 2003.

Chen et al., "A small molecule that directs differentiation of human ESCs into the pancreatic lineage," *Nat. Chem. Biol.*, 5(4):258-265, Apr. 2009.

Chung et al., "Mitochondrial oxidative metabolism is required for the cardiac differentiation of stem cells," *Nat. Clin. Pract. Cardiovasc. Med.*, 4 Suppl 1, S60-67 Feb. 2007.

Daheron et al., "LIF/STAT3 signaling fails to maintain self-renewal of human embryonic stem cells," *Stem Cells*, 22(5):770-778, 2004.

Demaison et al., "High-level transduction and gene expression in hematopoietic repopulating cells using a human immunodeficiency [correction of immunodeficiency] virus type 1-based lentiviral vector containing an internal spleen focus forming virus promoter," *Hum. Gene Ther.*, 13(7):806-813, May 2002.

Evans and Kaufman, "Establishment in culture of pluripotential cells from mouse embryos," *Nature*, 292(5819):154-156, Jul. 1981.

Faustino et al., "Genomic chart guiding embryonic stem cell cardiopoiesis ," *Genome Biol.*, 9(1):R6, Jan. 2008.

Felgner et al., "Enhanced gene delivery and mechanism studies with a novel series of cationic lipid formulations," *J. Biol. Chem.*, 269(4):2550-2561, Jan. 1994.

Finkel and Holbrook, "Oxidants, oxidative stress and the biology of ageing," *Nature*, 408(6809):239-247, Nov. 2000.

Flotte et al., "Stable in vivo expression of the cystic fibrosis transmembrane conductance regulator with an adeno-associated virus vector," *Proc. Natl. Acad. Sci. USA*, 90(22):10613-10617, Nov. 1993.

Fujii and Martin, "Incorporation of teratocarcinoma stem cells into blastocysts by aggregation with cleavage-stage embryos," *Dev. Biol.*, 74(1): 239-244, Jan. 1980.

GenBank® GI No. 109659099, Accession No. BC117435, "*Homo sapiens* POU class 5 homeobox 1, mRNA (cDNA clone MGC:151044 IMAGE:40125986), complete cds," Jul. 17, 2007, 2 pages.

GenBank® GI No. 12652778, Accession No. BC000141, "*Homo sapiens* v-myc myelocytomatosis viral oncogene homolog (avian), mRNA (cDNA clone MGC:5183 IMAGE:2985844), complete cds," Sep. 13, 2007, 3 pages.

GenBank® GI No. 163659904, Accession No. NM_000618, "*Homo sapiens* insulin-like growth factor 1 (somatomedin C) (IGF1), transcript variant 4, mRNA," Jul. 21, 2010, 5 pages.

GenBank® GI No. 188595715, Accession No. NM_001127500, "*Homo sapiens* met proto-oncogene (hepatocyte growth factor receptor) (MET), transcript variant 1, mRNA," Jul. 18, 2010, 7 pages.

GenBank® GI No. 20987475, Accession No. BC029923, "*Homo sapiens* Kruppel-like factor 4 (gut), mRNA (cDNA clone MGC:34918 IMAGE:5111134), complete cds," Jul. 15, 2006, 3 pages.

GenBank® GI No. 255090638, Accession No. GQ351295, "*Homo sapiens* fibroblast growth factor 10 (FGF10) mRNA, complete cds," Aug. 9, 2009, 1 page.

GenBank® GI No. 291190799, Accession No. NM_002054.3, "*Homo sapiens* glucagon (GCG), mRNA," Sep. 26, 2010, 4 pages.

GenBank® GI No. 33869633, Accession No. BC013923, "*Homo sapiens* SRY (sex determining region Y)-box 2, mRNA (cDNA clone MGC:2413 IMAGE:2823424), complete cds," Jul. 15, 2006, 2 pages.

GenBank® GI No. 33872076, Accession No. BC028566, "*Homo sapiens* lin-28 homolog (C. elegans), mRNA (cDNA clone MGC:15037 IMAGE:3841184), complete cds," Jun. 19, 2006, 4 pages.

GenBank® GI No. 71043476, Accession No. BC099704.1, "*Homo sapiens* Nanog homeobox pseudogene 8, mRNA (cDNA clone MGC:119250 IMAGE:40004920), complete cds," Nov. 7, 2006, 3 pages.

Hasegawa et al., "The use of a tropism-modified measles virus in folate receptor-targeted virotherapy of ovarian cancer," *Clin. Cancer Res.*, 12(20 Pt1):6170-6178, Oct. 2006.

Hodgson et al., "Stable benefit of embryonic stem cell therapy in myocardial infarction," *Am. J. Physiol. Heart Circ. Physiol.*, 287(2):H471-479, Aug. 2004.

Huangfu et al., "Induction of pluripotent stem cells from primary human fibroblasts with only Oct4 and Sox2," *Nat Biotechnol.*, 26(11):1269-1275, print Nov. 2008, Epub Oct. 2008.

Ikeda et al., "Continuous high-titer HIV-1 vector production," *Nat. Biotechnol.*, 21(5):569-572, print May 2003, Epub Apr. 2003.

Ikeda et al., "Gene transduction efficiency in cells of different species by HIV and EIAV vectors," *Gene Ther.*, 9(14):932-938, Jul. 2002.

Ikeda et al., "Influence of gag on human immunodeficiency virus type 1 species-specific tropism," *J. Virol.*, 78(21):11816-11822, Nov. 2004.

Kaplitt et al., "Long-term gene expression and phenotypic correction using adeno-associated virus vectors in the mammalian brain," *Nat. Genet.*, 8(2):148-154, Oct. 1994.

Kay et al., "Gene therapy," *Proc. Natl. Acad. Sci. USA*, 94(24):12744-12746, Nov. 1997.

Kootstra et al., "Abrogation of postentry restriction of HIV-1-based lentiviral vector transduction in simian cells," *Proc. Natl. Acad. Sci. USA*, 100(3):1298-1303, print Feb. 2003, Epub Jan. 2003.

Mali et al., "Improved Efficiency and Pace of Generating Induced Pluripotent Stem Cells from Human Adult and Fetal Fibroblasts," *Stem Cells*, 2008, 26:1998-2005.

Martin, "Isolation of a pluripotent cell line from early mouse embryos cultured in medicum conditioned by teratocarcinoma stem cells," *Proc. Natl. Acad. Sci. USA*, 78(12):7634-7638, Dec. 1981.

Martinez-Fernandez et al., "c-MYC independent nuclear reprogramming favors cardiogenic potential of induced pluripotent stem cells," *J Cardiovasc Transl Res.*, 3(1):13-23, Feb. 2010.

Martinez-Fernandez et al., "iPS programmed without c-MYC yield proficient cardiogenesis for functional heart chimerism," *Circ Res.*, 105(7):648-656, print Sep. 2009, Epub Aug. 2009.

Nagano and Fraser, "No-nonsense functions for long noncoding RNAs," *Cell*, 145(2):178-181, Apr. 2011.

Nagy et al., "Embryonic stem cells alone are able to support fetal development in the mouse," Development, 110(3):815-821, Nov. 1990.

Narazaki et al., "Directed and Systematic Differentiation of Cardiovascular Cells From Mouse Induced Pluripotent Stem Cells," *Circulation*, 118:498-506, 2008.

Negri et al., "Successful immunization with a single injection of non-integrating lentiviral vector," *Mol. Ther.*, 15(9):1716-1723, print Sep. 2007, Epub Jun. 2007.

Nelson et al., "CXCR4+/FLK-1+ biomarkers select a cardiopoietic lineage from embryonic stem cells," *Stem Cells*, 26(6):1464-1474, print Jun. 2008, Epub Mar. 2008.

Nelson et al., "Induced pluripotent reprogramming from promiscuous human stemness-related factors," *Clin Transl Sci.*, 2(2):118-126, Apr. 2009.

Nelson et al., "KCNJ11 knockout morula re-engineered by stem cell diploid aggregation," *Phil. Trans. R. Soc. B.*, 364(1514):269-276, Jan. 2009.

Nelson et al., "Lineage specification of Flk-1+ progenitors is associated with divergent Sox7 expression in cardiopoiesis," *Differentiation*, 77(3):248-255, Mar. 2009.

(56) References Cited

OTHER PUBLICATIONS

Nelson et al., "Repair of acute myocardial infarction by human stemness factors induced pluripotent stem cells," *Circulation*, 120(5):408-416, print, Aug. 2009, Epub Jul. 2009.
Noser et al., "Cyclosporine increases human immunodeficiency virus type 1 vector transduction of primary mouse cells," *J. Virol.*, 80(15):7769-7774, Aug. 2006.
Noser et al., "The RAS/Raf1/MEK/ERK signaling pathway facilitates VSV-mediated oncolysis: implication for the defective interferon response in cancer cells," *Mol. Ther.*, 15(8):1531-1536, print Aug. 2007, Epub May 2007
Ohmine et al., "Induced pluripotent stem cells from GMP-grade hematopoietic progenitor cells and mononuclear myeloid cells," *Stem Cell Res Ther.*, 2(6):46, doi: 10.1186/scrt87, 12 pages, Nov. 2011.
Ohmine et al., "Reprogrammed keratinocytes from elderly type 2 diabetes patients suppress senescence genes to acquire induced pluripotency," *Aging*, 4(1):60-73, Jan. 2012.
Palmowski et al., "Intravenous injection of a lentiviral vector encoding NY-ESO-1 induces an effective CTL response," *J. Immunol.*, 172(3):1582-1587, Feb. 2004.
Perez-Terzic et al., "Stem cells transform into a cardiac phenotype with remodeling of the nuclear transport machinery," *Nat. Clin. Pract. Cardiovasc. Med.*, 4 Suppl 1, S68-76, Feb. 2007.
Perez-Terzic et al., "Structural adaptation of the nuclear pore complex in stem cell-derived cardiomyocytes," *Circ. Res.*, 92(4):444-452, print Mar. 2003, Epub Jan. 2003.
Philpott et al., "A p5 integration efficiency element mediates Rep-dependent integration into AAVS1 at chromosome 19," *Proc. Natl. Acad. Sci. USA*, 99(19):12381-12385, Sep. 2002.
Philpott et al., "Efficient integration of recombinant adeno-associated virus DNA vectors requires a p5-rep sequence in cis," *J. Virol.*, 76(11):5411-5421, Jun. 2002.
Qi and Pei, "The magic of four: induction of pluripotent stem cells from somatic cells by Oct4, Sox2, Myc and Klf4," *Cell Research*, 17(7):578-580, Jul. 2007.
Rajasingh et al., "Cell-free embryonic stem cell extract-mediated derivation of multipotent stem cells from NIH3T3 fibroblasts for functional and anatomical ischemic tissue repair," *Circ Res.*, 102(11):e107-117 print Jun. 2008, Epub May 2008.
Ramiya et al., "Reversal of insulin-dependent diabetes using islets generated in vitro from pancreatic stem cells," *Nat. Med.*, 6(3):278-282, Mar. 2000.
Relander et al., "Gene transfer to repopulating human CD34+ cells using amphotropic-, GALV-, or RD114-pseudotyped HIV-1-based vectors from stable producer cells," *Mol. Ther.*, 11(3):452-459, Mar. 2005.
Saenz et al., "Unintegrated lentivirus DNA persistence and accessibility to expression in nondividing cells: analysis with class I integrase mutants," *J. Virol.*, 78(6):2906-2290, Mar. 2004.
Sakuma et al., "Characterization of retroviral and lentiviral vectors pseudotyped with xenotropic murine leukemia virus-related virus envelope glycoprotein," *Hum. Gene Ther.*, 21(12):1665-1673, print Dec. 2010, Epub Sep. 2010.
Sakuma et al , "Inhibition of HIV-1 replication by simian restriction factors, TRIM5alpha and APOBEC3G," *Gene Ther.*, 14(2):185-189, print Jan. 2007, Epub Aug. 2006.
Schenke-Layland et al, "Reprogrammed mouse fibroblasts differentiate into cells of the cardiovascular and hematopoietic lineages," *Stem Cells*, 26(6):1537-1546, print Jun. 2008, Epub May 2008.
Solter and Knowles, "Monoclonal antibody defining a stage-specific mouse embryonic antigen (SSEA-1)," *Proc. Natl. Acad. Sci. USA*, 75(11):5565-5569, Nov. 1978.
Stewart, "Aggregation between teratocarcinoma cells and preimplantation mouse embryos," *J. Embryol. Exp. Morphol.*, 58:289-302, Aug. 1980.
Strang et al., "Characterization of HIV-1 vectors with gammaretrovirus envelope glycoproteins produced from stable packaging cells," *Gene Ther.*, 11(7):591-598, Apr. 2004.

Strang et al., "Human immunodeficiency virus type 1 vectors with alphavirus envelope glycoproteins produced from stable packaging cells," *J. Virol.*, 79(3):1765-1771, Feb. 2005.
Takahashi et al., "Induction of Pluripotent Stem Cells from Adult Human Fibroblasts by Defined Factors," *Cell*, 131:861-872, Nov. 2007.
Tateishi et al., "Stemming heart failure with cardiac- or reprogrammed-stem cells," *J Cell Mol Med.*, 12(6A):2217-2232, print Dec. 2008, Epub Aug. 2008.
Thatava et al., "Differentiation of Diabetic Patient-Specific iPS Cells into Insulin-Secreting Cells," *Molecular Therapy*, vol. 19, p. S121, abstract 311, May 2011.
Thatava et al., "Generation of glucose-responsive insulin-secreting cells from Type 1 Diabetes-specific induced pluripotent stem cells," 2011 Meeting on Stem Cell Engineering & Cell-based Therapies: Apr. 7-10, 2011, Cold Spring Harbor Laboratory, 25 pages.
Thatava et al., "Generation of insulin-secreting cells from human induced pluripotent stem cells," *Molecular Therapy*, vol. 18, p. S246, abstract 633, May 2010.
Thatava et al., "Generation of insulin-secreting cells from human induced pluripotent stem cells," *American Society of Gene and Cell Therapy* 13th Annual Meeting, Washington, DC USA, May 19-22, 2010, 18 pages.
Thatava et al., "Pancreatic differentiation of diabetic patient-specific iPS cells," *American Society of Gene and Cell Therapy*,14th Annual Meeting, Seattle, WA, USA, May 18-21, 2011, 20 pages.
Thomson et al., "Embryonic stem cell lines derived from human blastocysts," *Science*, 282(5391):1145-1147, Nov. 1998.
Wernig et al., "c-Myc is dispensable for direct reprogramming of mouse fibroblasts," *Cell Stem Cell*, 2(1):10-12 print Jan. 2008, Epub Dec. 2007.
Wolf and Goff, "TRIM28 mediates primer binding site-targeted silencing of murine leukemia virus in embryonic cells," *Cell*, 131(1):46-57, Oct. 2007.
Wood et al., "Non-injection methods for the production of embryonic stem cell-embryo chimaeras," *Nature*, 365(6441):87-89, Sep. 1993.
Yamada et al., "Embryonic stem cell therapy of heart failure in genetic cardiomyopathy," *Stem Cells*, 26:2644-2653, Oct. 2008.
Yamanaka, "Pluripotency and nuclear reprogramming," *Philos Trans R Soc Lond B Biol Sci.*, 363(1500):2079-2087, Jun. 2008.
Yu et al., "Induced pluripotent stem cell lines derived from human somatic cells," *Science*, 318(5858):1917-1920, print Dec. 2007, Epub Nov. 2007.
Yuasa and Fukuda, "Recent advances in cardiovascular regenerative medicine: the induced pluripotent stem cell era," *Expert Rev Cardiovasc Ther.*, 6(6):803-810, Jul. 2008.
Zufferey et al., "Multiply attenuated lentiviral vector achieves efficient gene delivery in vivo," Nat. Biotechnol., 15(9):871-875, Sep. 1997.
European Search Report for Application No. 09805666.6, mailed Jun. 22, 2012, 11 pages.
International Preliminary Report on Patentability for PCT/US2009/053314, issued Feb. 8, 2011, 6 pages.
International Search Report and Written Opinion in International Application No. PCT/US2009/053314, mailed Mar. 3, 2010, 15 pages.
Office Action in U.S. Appl. No. 13/553,064, mailed Jul. 25, 2013, 6 pages.
Office Action in U.S. Appl. No. 13/058,154, mailed Aug. 28, 2013, 13 pages.
Office Action in U.S. Appl. No. 13/058,154, mailed Mar. 25, 2014, 16 pages.
Office Action in U.S. Appl. No. 13/553,064, mailed Mar. 27, 2014, 11 pages.
Office Action in U.S. Appl. No. 13/058,154, mailed Jul. 15, 2014, 19 pages.
Stadtfeld, "Defining molecular cornerstones during fibroblast to iPS cell reprogramming in mouse," Cell Stem Cell., 2 (3):230-240, Epub Feb. 14, 2008.
Stadtfeld, "Induced pluripotent stem cells generated without viral integration," Science, 322(5903):945-949, Nov. 7, 2008.

(56) References Cited

OTHER PUBLICATIONS

Office Action in U.S. Appl. No. 13/058,154, mailed Mar. 20, 2015, 15 pages.
Banasik et al., "Integrase-defective lentiviral vectors: progress and applications," Gene Ther., 17(2):150-157, Epub Oct. 22, 2009.
Fusaki et al., "Efficient induction of transgene-free human pluripotent stem cells using a vector based on Sendai virus, an RNA virus that does not integrate into the host genome," Proc Jpn Acad Ser B Phys Biol Sci., 85(8):348-362, 2009.
Philippe et al., "Lentiviral vectors with a defective integrase allow efficient and sustained transgene expression in vitro and in vivo," Proc Natl Acad Sci U S A., 103(47):17684-17689, Epub Nov. 9, 2006.
Yáñez-Muñoz et al., "Effective gene therapy with nonintegrating lentiviral vectors," Nat Med., 12(3):348-353, Mar. 2006.
Yu et al., "Transient gene expression mediated by integrase-defective retroviral vectors," Biochem Biophys Res Commun., 368(4):942-947, Epub Feb. 13, 2008.
Office Action in U.S. Appl. No. 13/058,154, dated Feb. 3, 2016, 22 pages.
D'Amour et al., "Efficient differentiation of human embryonic stem cells to definitive endoderm," Nat. Biotechnol., 23(12):1534-1541, Dec. 2005.
Bilic and Belmonte, "Concise Review: Induced Pluripotent Stem Cells Versus Embryonic Stem Cells: Close Enough or Yet Too Far Apart?" Stem Cell Res., 33:33-41, 2012.
International Preliminary Report on Patentability for PCT/US2015/014377, dated Aug. 18, 2016, 6 pages.
International Search Report and Written Opinion for PCT/US2015/014377, dated Apr. 17, 2015, 11 pages.
Jiang et al., "Parkin controls dopamine utilization in human midbrain dopaminergic neurons derived from induced pluripotent stem cells," Nat Commun., 3:668, 9 pages, Feb. 7, 2012.
Karakikes et al., "Small molecule-mediated directed differentiation of human embryonic stem cells toward ventricular cardiomyocytes," Stem Cells Transl Med., 3(1):18-31. Epub Dec. 9, 2013, Jan. 2014.
Kim et al., "Epigenetic memory in induced pluripotent stem cells," Nature., 467(7313):285-290, Sep. 16, 2010.
Kroon et al., "Pancreatic endoderm derived from human embryonic stem cells generates glucose-responsive insulin-secreting cells in vivo," *Nat Biotechnol.*, 26(4):443-452, Epub Feb. 20, 2008.
Kudva et al., "Transgene-free disease-specific induced pluripotent stem cells from patients with type 1 and type 2 diabetes," *Stem Cells Transl Med.*, 1(6):451-461, Epub May 30, 2012.
Lister et al., "Hotspots of aberrant epigenomic reprogramming in human induced pluripotent stem cells," *Nature.*, 471(7336): 68-73, Mar. 3, 2011.
Office Action in U.S. Appl. No. 13/058,154, dated Dec. 8, 2014, 13 pages.
Yu et al., "Hepatocyte-like cells differentiated from human induced pluripotent stem cells: relevance to cellular therapies," Stem Cell Res., 9(3):196-207, Epub Jun. 28, 2012.

Figure 9
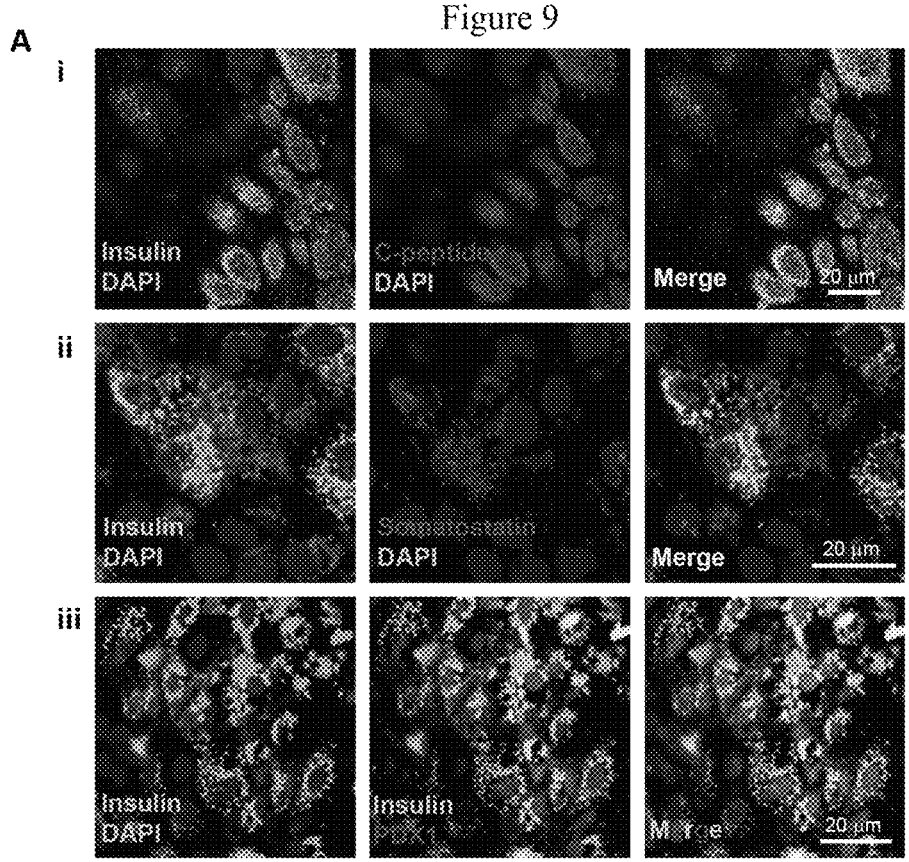
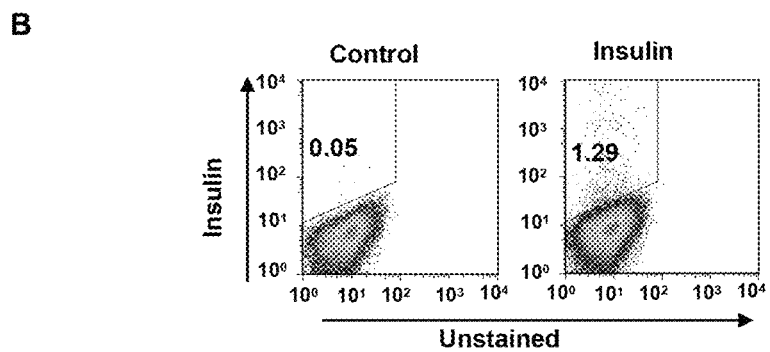
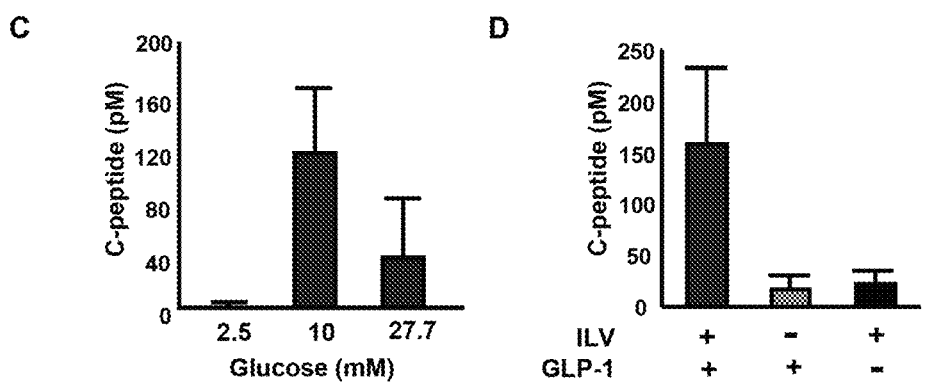

Figure 11
A
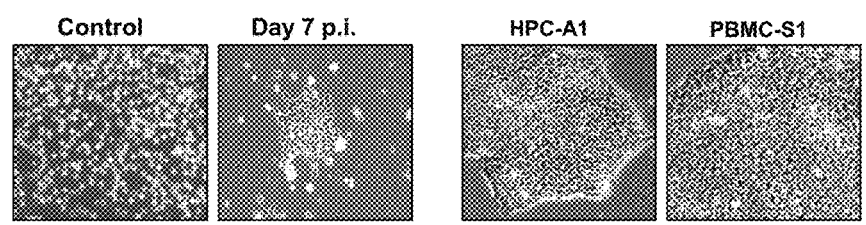
B
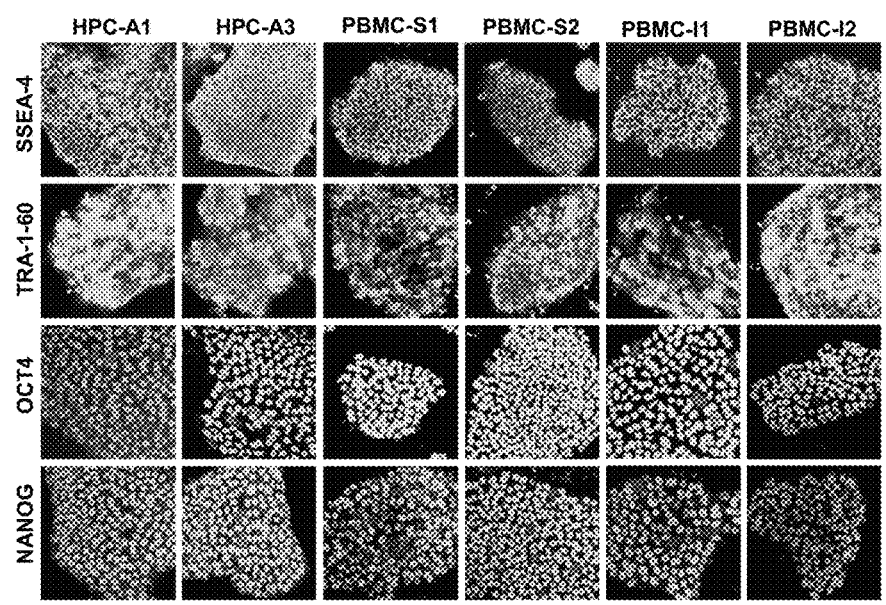

Figure 16
A
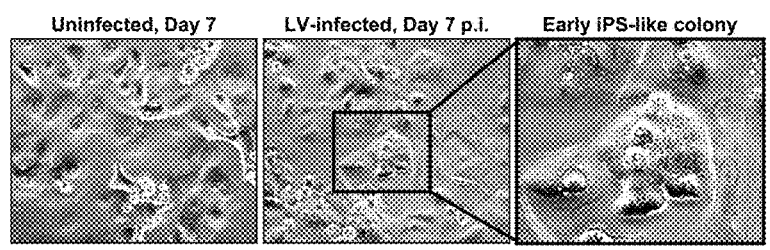
B
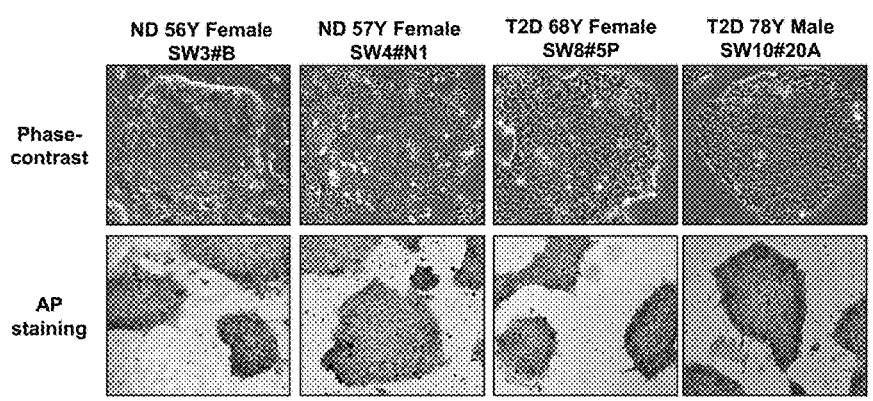
C
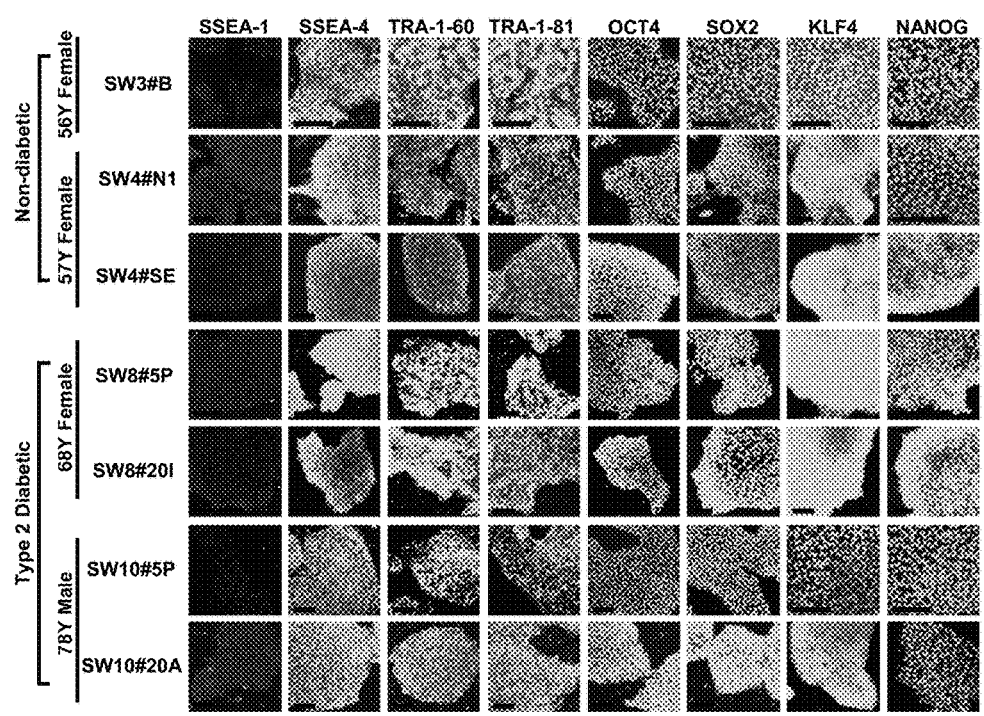

Figure 20
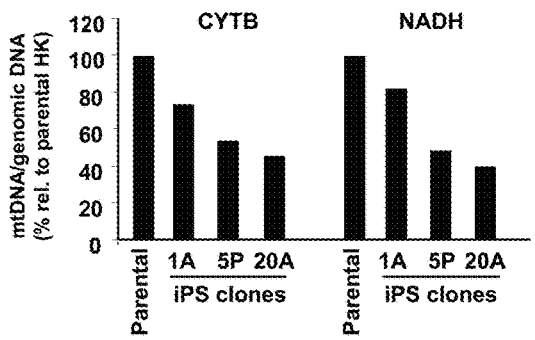
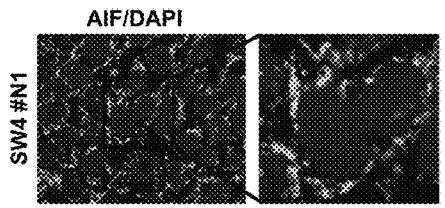
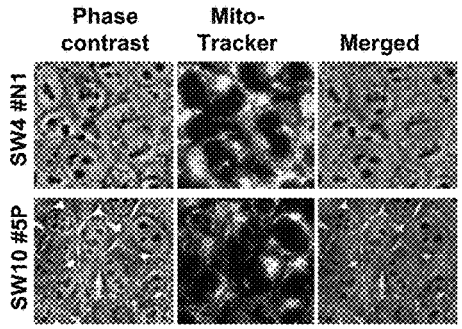
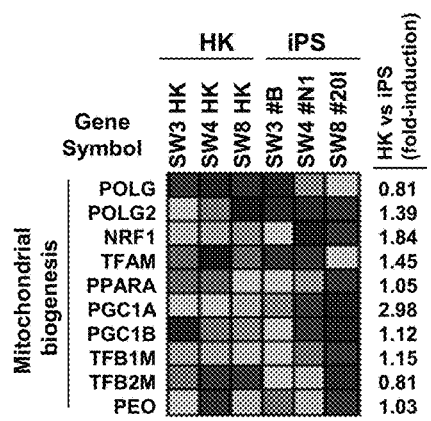
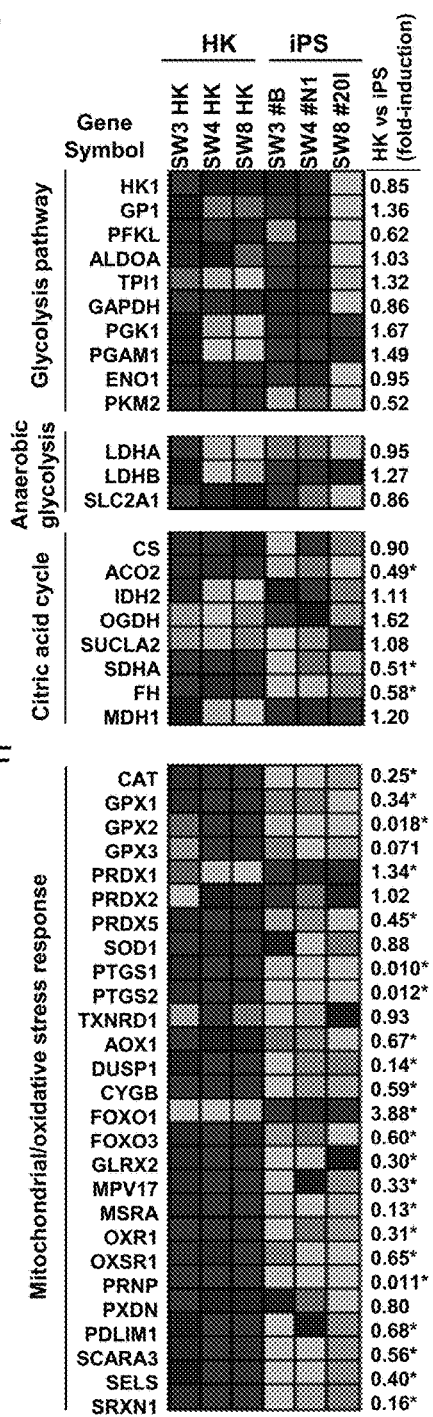

DIFFERENTIATING INDUCED PLURIPOTENT STEM CELLS INTO GLUCOSE-RESPONSIVE, INSULIN-SECRETING PROGENY

CROSS-REFERENCE TO RELATED APPLICATIONS

This application is a continuation of U.S. application Ser. No. 13/553,064, filed Jul. 19, 2012, which claims the benefit of U.S. Provisional Application Ser. No. 61/510,818, filed Jul. 22, 2011. The disclosure of the prior applications are considered part of (and are incorporated by reference in) the disclosure of this application.

BACKGROUND

1. Technical Field

This document relates to methods and materials involved in differentiating induced pluripotent stem (iPS) cells into glucose-responsive, insulin-secreting progeny. For example, this document relates to the use of indolactam V (ILV) and glucagon like peptide-1 (GLP-1) to produce glucose-responsive, insulin-secreting progeny from iPS cells.

2. Background Information

Stem cells are characterized by the ability of self-renewal and differentiation into a diverse range of cell types. The two broad types of mammalian stem cells are embryonic stem (ES) cells and adult stem cells. Adult stem cells or progenitor cells replenish specialized cells to repair or maintain regenerative organs. Most adult stem cells are lineage-restricted and generally referred to by their tissue origin, such as adipose-derived stem cells. ES cell lines are derived from the epiblast tissue of the inner cell mass of a blastocyst or early morula stage embryos. ES cells are pluripotent and give rise to derivatives of the three germinal layers, i.e., the ectoderm, endoderm, and mesoderm.

SUMMARY

This document provides methods and materials related to differentiating iPS cells into glucose-responsive, insulin-secreting progeny. For example, this document provides methods and material for using ILV and GLP-1 to produce glucose-responsive, insulin-secreting progeny from iPS cells. As described herein, culturing iPS cells in the presence of a collection of agents that include ILV and GLP-1 can result in the production of glucose-responsive, insulin-producing cells. For example, an ILV and GLP-1-enriched pancreatogenic cocktail can be used under feeder cell-free conditions to produce glucose-responsive, insulin-producing cells from human iPS cells. Autologous iPS cell derivation and iPS cell differentiation into insulin-producing cells can allow modeling of patient-specific disease pathogenesis and can lead to personalized approaches for type 1 diabetes cell therapy with iPS-derived islet-like cells.

In general, one aspect of this document features a method for obtaining a population of glucose-responsive, insulin-secreting cells from a population of induced pluripotent stem cells. The method comprises, or consists essentially of, culturing the induced pluripotent stem cells with medium comprising indolactam V and glucagon like peptide-1 under conditions to obtain the population of glucose-responsive, insulin-secreting cells. The medium can lack serum. The medium can lack feeder cells. The medium can lack non-human feeder cells. The induced pluripotent stem cells can be induced pluripotent stem cells that were obtained using one or more polypeptides or nucleic acid encoding the one or more polypeptides selected from the group consisting of a Oct3/4 polypeptide, a Sox family polypeptide, a Klf family polypeptide, a Myc family polypeptide, a Nanog polypeptide, and a Lin28 polypeptide. The induced pluripotent stem cells can be induced pluripotent stem cells that were induced from somatic cells. The somatic cells can be selected from the group consisting of skin, lung, heart, stomach, brain, liver, blood, kidney, and muscle cells. The induced pluripotent stem cells can comprise exogenous nucleic acid encoding a human Oct4 polypeptide, a human Sox2 polypeptide, a human Klf4 polypeptide, and a human c-Myc polypeptide. The glucose-responsive, insulin-secreting cells can secrete greater than 50 pM of C peptide per hour when in culture in the presence of about 10 mM of glucose. The glucose-responsive, insulin-secreting cells can secrete greater than 200 pM of C peptide per hour when in culture in the presence of about 10 mM of glucose. The glucose-responsive, insulin-secreting cells can secrete between about 50 and 250 pM of C peptide per hour when in culture in the presence of about 10 mM of glucose. The glucose-responsive, insulin-secreting cells can be human cells. The medium can comprise greater than 300 nM of indolactam V. The medium can comprise greater than 55 nM of glucagon like peptide-1. The culturing can be performed for more than 25 days. In another aspect, this document features a population of glucose-responsive, insulin-secreting cells derived from induced pluripotent stem cells, wherein the glucose-responsive, insulin-secreting cells are produced by culturing the induced pluripotent stem cells with medium comprising indolactam V and glucagon like peptide-1 under conditions that result in the formation of the population of glucose-responsive, insulin-secreting cells. The medium can comprise greater than 300 nM of indolactam V. The medium can comprise greater than 55 nM of glucagon like peptide-1. The culturing can be performed for more than 25 days. The population of glucose-responsive, insulin-secreting cells can secrete greater than 50 pM of C peptide per hour when in culture in the presence of about 10 mM of glucose. The population of glucose-responsive, insulin-secreting cells can secrete greater than 200 pM of C peptide per hour when in culture in the presence of about 10 mM of glucose. The population of glucose-responsive, insulin-secreting cells can secrete between about 50 and 250 pM of C peptide per hour when in culture in the presence of about 10 mM of glucose. The glucose-responsive, insulin-secreting cells can be human cells.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

iPS cells were treated with activin A and Wnt3a for one day, followed by activin A with 2% FBS for two days. iPS-derived cells were immunostained with antibodies against SOX17 (green stain was used) and FOXA2 (red stain was used). Cells were counterstained by DAPI. Bars indicate 20 μm. (C) Flow cytometric analyses of iPS-derived definitive endoderm cells. iPS-derived definitive endoderm cells were dissociated and stained with anti-SOX17 antibody. Staining with the secondary antibody alone was used as a control. (D) iPS-derived definitive endoderm cells were treated with FGF10, CYC, RA, and ILV for induction of pancreatic endoderm and immunofluorescence analysis was performed to detect, PDX1 (red stain was used), NEUROD1 (red stain was used), and NGN3 (red stain was used).

Figure 6:
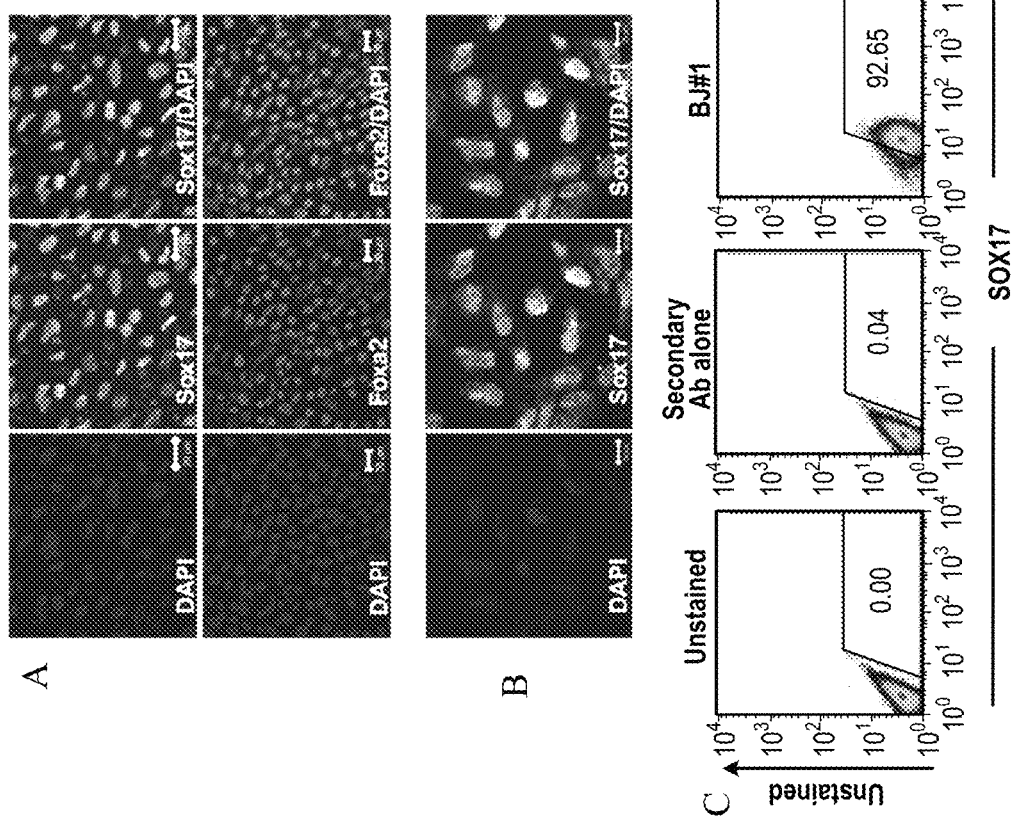

FIG. 6. Differentiation of BJ#1 and BJ#SA Clones into Definitive Endoderm Cells. BJ#1 and BJ#SA cells were treated with activin A and Wnt3a for one day, followed by activin A stimulation in the presence of 2% FBS for two days for generation of definitive endoderm cells. (A) BJ#SA derived definitive endoderm cells were immunostained with antibodies against SOX17 (a green stain was used) and FOXA2 (a red stain was used). (B) BJ#1 derived definitive endoderm cells were stained with antibody against SOX17. Cells were counterstained by DAPI. Bars indicate 20 mm. (C) Flow cytometric analyses of iPS-derived definitive endoderm cells. iPS-derived definitive endoderm cells were dissociated and stained with anti-SOX17 antibody. Staining with the secondary antibody alone was used as a control.

Figure 7:
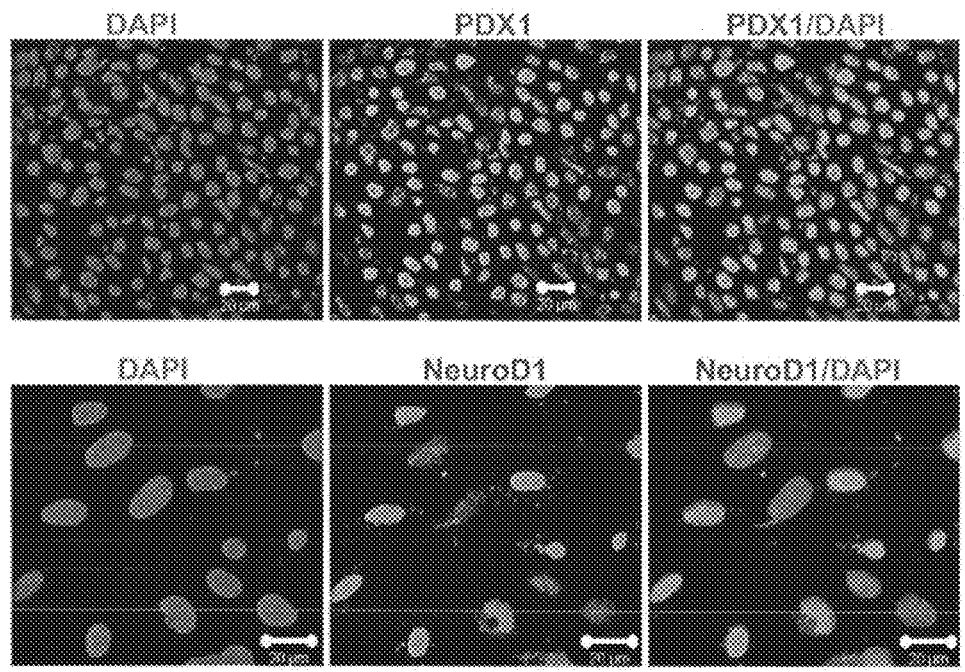

FIG. 7. Efficient Differentiation of iPS Cells into Pancreatic Endoderm Cells. iPS-derived definitive endoderm cells were treated with FGF10, CYC, RA, and ILV for induction of pancreatic endoderm. On day 17 of differentiation, immunofluorescence analysis was performed to detect pancreatic endoderm markers, PDX1 (a red stain was used) and NEUROD1 (a red stain was used) from BJ#SA-derived cells.

Figure 8:
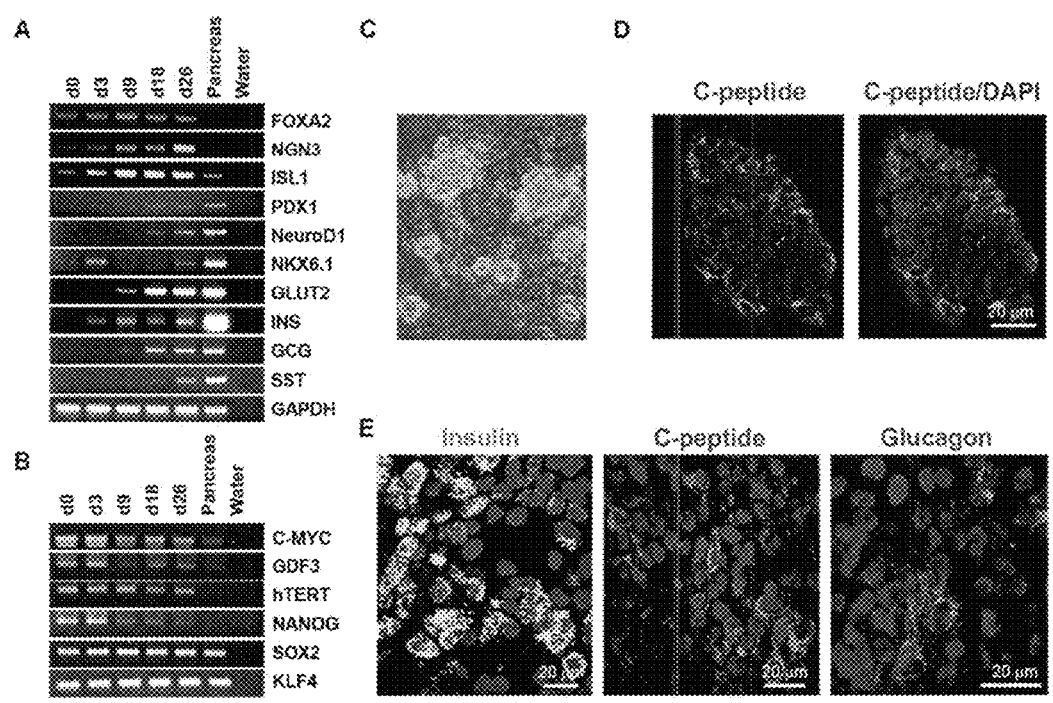

FIG. 8. Successful Differentiation of Human iPS Cells into Pancreatic Hormone-expressing Cells. (A) Induction of stage-specific pancreatic genes through guided differentiation. RT-PCR analysis was performed to determine the expression of key pancreatic genes at different stages of differentiation. Undifferentiated human iPS cells (d0), definitive endoderm cells after treatment with activin A and Wnt3a (d3), foregut endoderm cells induced with FGF10 and CYC (d9), pancreatic endoderm cells were generated after exposure with FGF10, RA, CYC, and ILV (d18) and islet-like clusters in presence of HGF, IGF, and GLP-1. Human pancreas RNA was used as a positive control. No template (water) was included as negative control. (B) Down-regulation of pluripotency-associated genes upon differentiation. RT-PCR analysis was performed to analyze the expression of pluripotency genes (c-MYC, GDF3, hTERT and NANOG) after stepwise differentiation. The same RNA samples as FIG. 8A were used. (C) Formation of islet-like clusters in HCF#1-derived cells upon differentiation. iPS-derived pancreatic endoderm were differentiated into islet-like cells with HGF, IGF, DAPT, and GLP-1. Prominent islet-like cluster formation was observed in HCF#1-derived cells. (D) Islet-like clusters expressed high levels of human C-peptide. (E) Detection of pancreatic hormones insulin, C-peptide and glucagon in iPS-derived islet-like cells. Immunofluorescence analysis identified iPS-derived islet-like cells which expressed insulin (green stain was used), C-peptide (red stain was used), and glucagon (red stain was used).

FIG. 9. Sustained PDX1 Expression and Glucose-Responsive C-Peptide Secretion by iPS-derived Islet-like Cells. (A) iPS-derived islet-like cells demonstrated beta cell characteristics. (i) Double-staining of iPS-derived islet-like cells revealed co-localization of insulin (green stain was used) and C-peptide (red stain was used), indicating de novo insulin synthesis. (ii) Some cells were double-positive for insulin (green stain was used) and somatostatin (red stain was used). (iii) Sustained PDX1 expression (red stain was used) in the iPS-derived insulin-producing cells after differentiation. Cells were counterstained with DAPI. (B) Flow cytometric analysis of iPS-derived islet-like cells for insulin expression. iPS-derived islet-like clusters were dissociated with TrypLE, and analyzed for insulin expression by an anti-human insulin antibody. Insulin staining was observed in HCF#1-derived islet-like clusters. (C) Glucose-responsive C-peptide secretion by the iPS-derived islet-like clusters. The islet-like clusters were sequentially exposed to low (2.5 mM), intermediate (10 mM), and high concentrations (27.7 mM) of glucose. Supernatants of HCF#1-derived islet-like cells were collected and analyzed for C-peptide secretion by ELISA. Error bars indicate standard deviation. (D) Glucose-responsive C-peptide secretion by HCF#1-derived islet-like clusters generated with pancreatogenic cocktails including GLP-1 and ILV (left), GLP-1 without ILV (middle), or ILV without GLP-1 (right). The islet-like clusters were sequentially exposed to low (2.5 mM), intermediate (10 mM), and high concentrations (27.7 mM) of glucose. Cumulative C-peptide secretion upon glucose stimulation with 10 mM and 27.7 mM were shown. Error bars indicate standard deviation.

Figure 10:
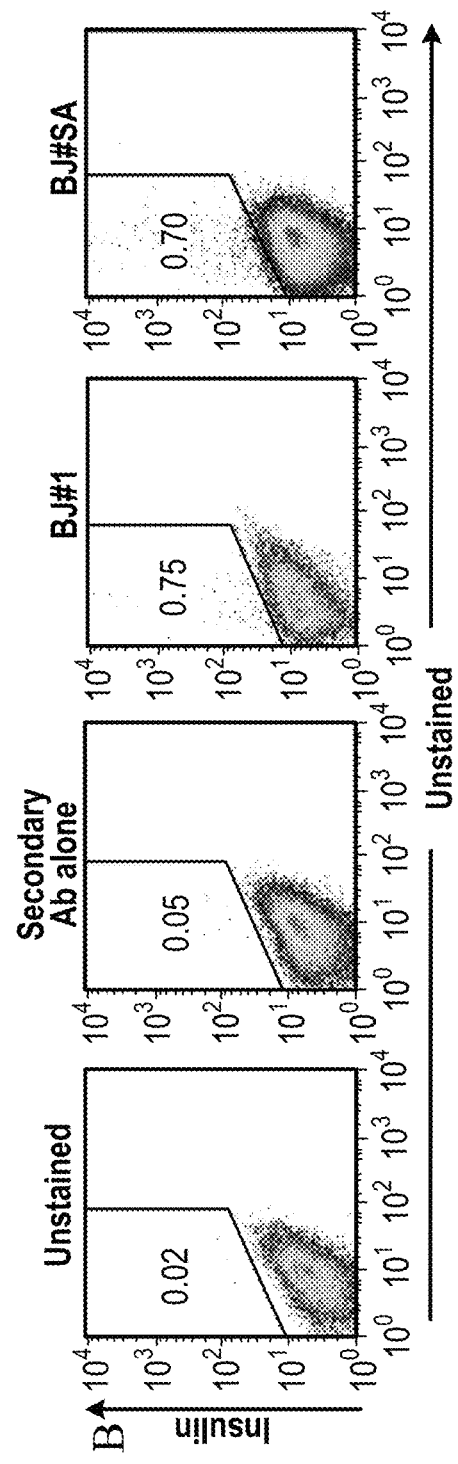

FIG. 10. Formation of Islet-like Clusters in BJ#1 and BJ#SA-derived Cells. iPS-derived pancreatic endoderm cells were differentiated into islet-like cells with HGF, IGF, DAPT and GLP-1. (A) Islet-like clusters formed in differentiated BJ#1 and BJ#SA cells. (B) Flow cytometric analysis of iPS-derived islet-like cells for insulin expression. iPS-derived islet-like clusters were dissociated with TrypLE, and analyzed for insulin expression by an anti-human insulin antibody. Insulin staining was observed in BJ#1 and BJ#SA-derived islet-like clusters.

FIG. 11. Reprogramming of human hematopoietic progenitor and peripheral blood mononuclear cells. (A) HPCs and PBMCs were cultured in a serum-free medium and transduced with lentiviral vectors expressing four stemness factors at an MOI of 5. Representative phase-contrast images of HPCs before transduction (left panel) and 7 day post-infection (left panel) are shown. Representative HPC- (left panel) and PBMC-(right panel) derived colonies with characteristic morphologies of reprogrammed cells are shown. (B) HPC and PBMC-derived iPSC clones were further characterized through immunocytochemistry analysis using a panel of antibodies against pluripotency-associated markers. All clones stained positive for the markers including SSEA-4, TRA-1-60, OCT4, and NANOG.

Figure 12:
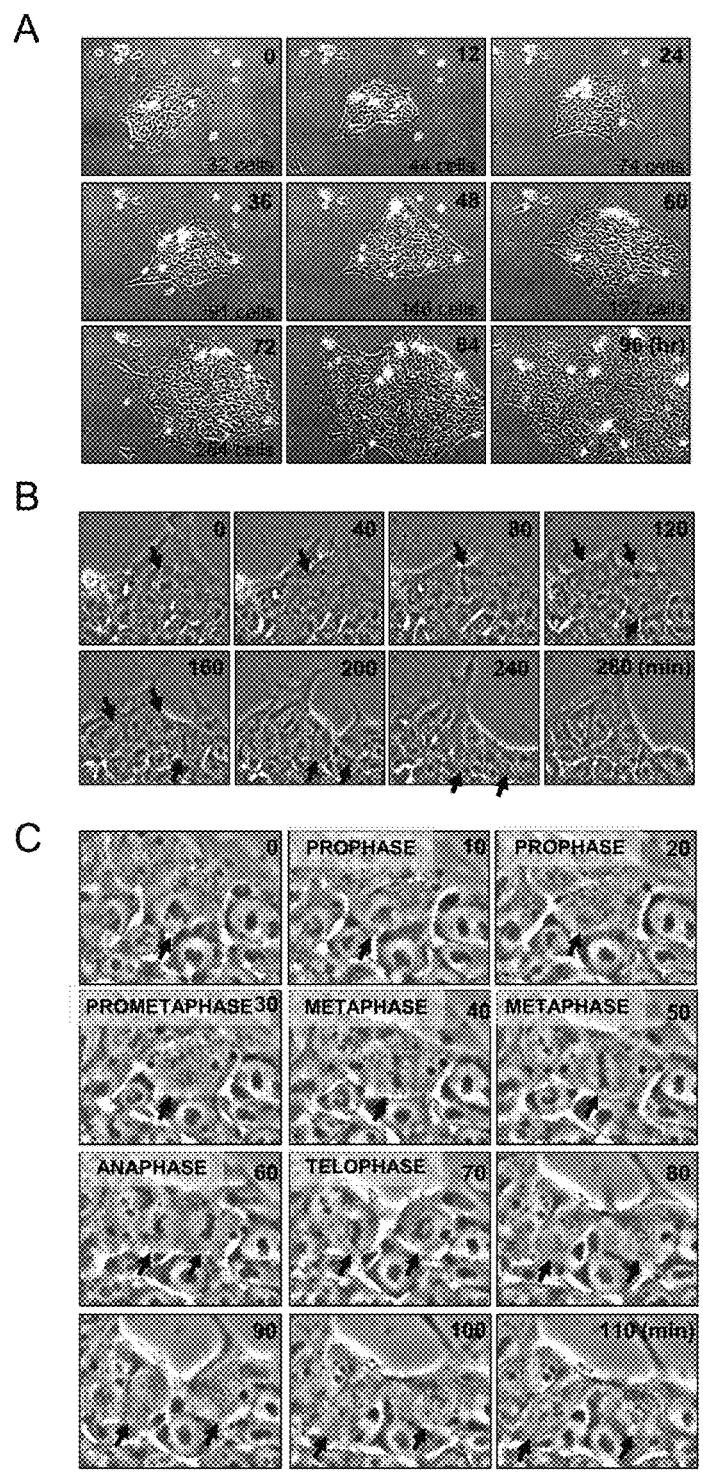

FIG. 12. Efficient expansion of HSC/PBMC-derived iPSC clones under feeder- and serum-free conditions. (A) Long-term time-lapse images of an iPSC #HPC-A1 colony were obtained using Nikon BioStation IMQ. Time is shown in hours in the upper right corner, and cell count is shown in the bottom right corner of each panel. (B) Frequent mitotic events were observed during time-lapse imaging. Dividing cells and daughter cells are indicated by downward pointing arrows and upward pointing arrows, respectively. Time is shown in minutes in the upper right corner of each panel. (C) High magnification images of a dividing cell at different stages of mitosis (prophase, prometaphase, metaphase, anaphase, and telophase) are indicated in arrows. Time is shown in minutes in the upper right corner of each panel.

Figure 13:
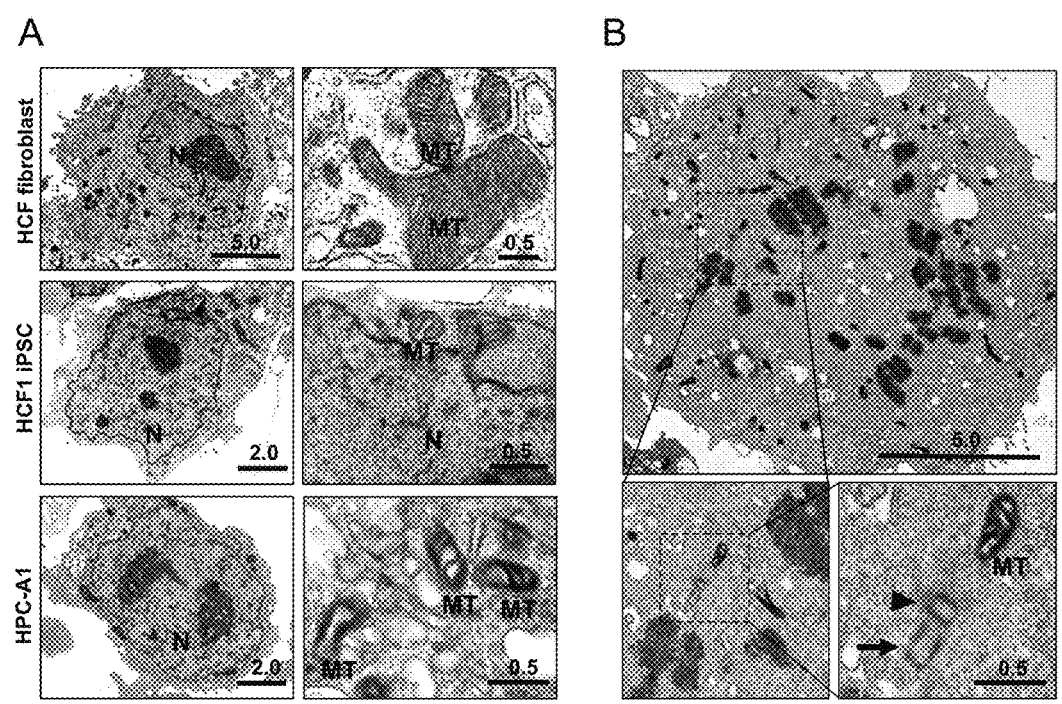

FIG. 13. Transmission electron microscopic images of blood-derived iPS cells. (A) Representative high-resolution electron micrographs of primary human fibroblasts (HCF fibroblast), HCF-derived (HCF1 iPS), and HPC-derived (HPC-A1) iPSCs are shown. Mitochondria (MT) and nucleus (N) structures are denoted in the micrographs. (B) Frequent mitotic events were observed in the blood-derived iPSCs. Mother and daughter centrioles are represented by the arrowhead and arrow symbols, respectively. Scale bars are represented in μm.

Figure 14:
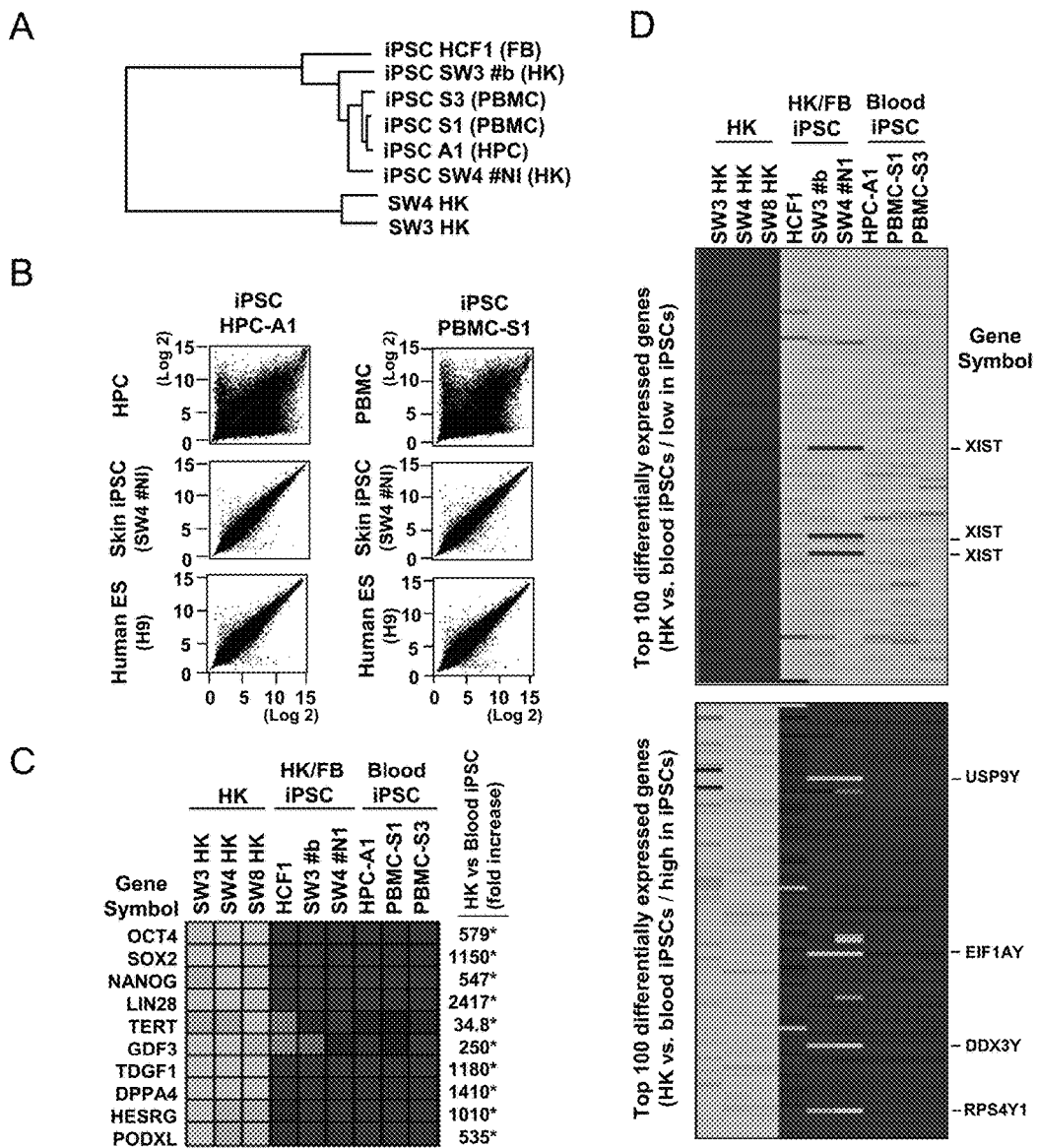

FIG. 14. Global gene expression profiles of blood-derived iPSCs. (A) Dendrogram describing the unsupervised hierarchal clustering of primary keratinocytes (SW3 HK and SW3 HK), and keratinocyte (HK)-, fibroblast (FB)-, HPC- and PBMC-derived iPSCs. (B) Genome-wide gene expression patterns of HPC- and PBMC-derived iPSC clones were compared with those of HPCs (GSM178554), PBMCs (GSM452255), verified epidermal keratinocyte-derived iPSCs (SW4#N1, upper panels), or embryonic stem cells (H9 cells, GSM190779). (C) Heatmap demonstrating the relative expression levels ((high—black; low—white) of pluripotency-associated genes in primary keratinocytes (HK) and iPS cells from HK, FB or blood cell sources. The changes in gene expression levels in blood-derived iPSCs, relative to those in HK cells, were calculated using the microarray data from three primary HK cells and three blood-derived iPSCs, and shown as fold-increase in iPSCs. Statistically significant changes are indicated by asterisks ($p<0.05$). (D) Heatmap showing the top 100 differentially expressed genes between non-reprogrammed HK and blood-derived iPSC clones (high—black; low—white). Highly expressed in non-reprogrammed cells and blood-derived iPSCs are shown in upper and lower panels, respectively. Genes with notable differences in gene expression patterns between HK/FB-derived and blood-derived iPSCs are indicated by the gene symbols on the right.

Figure 15:
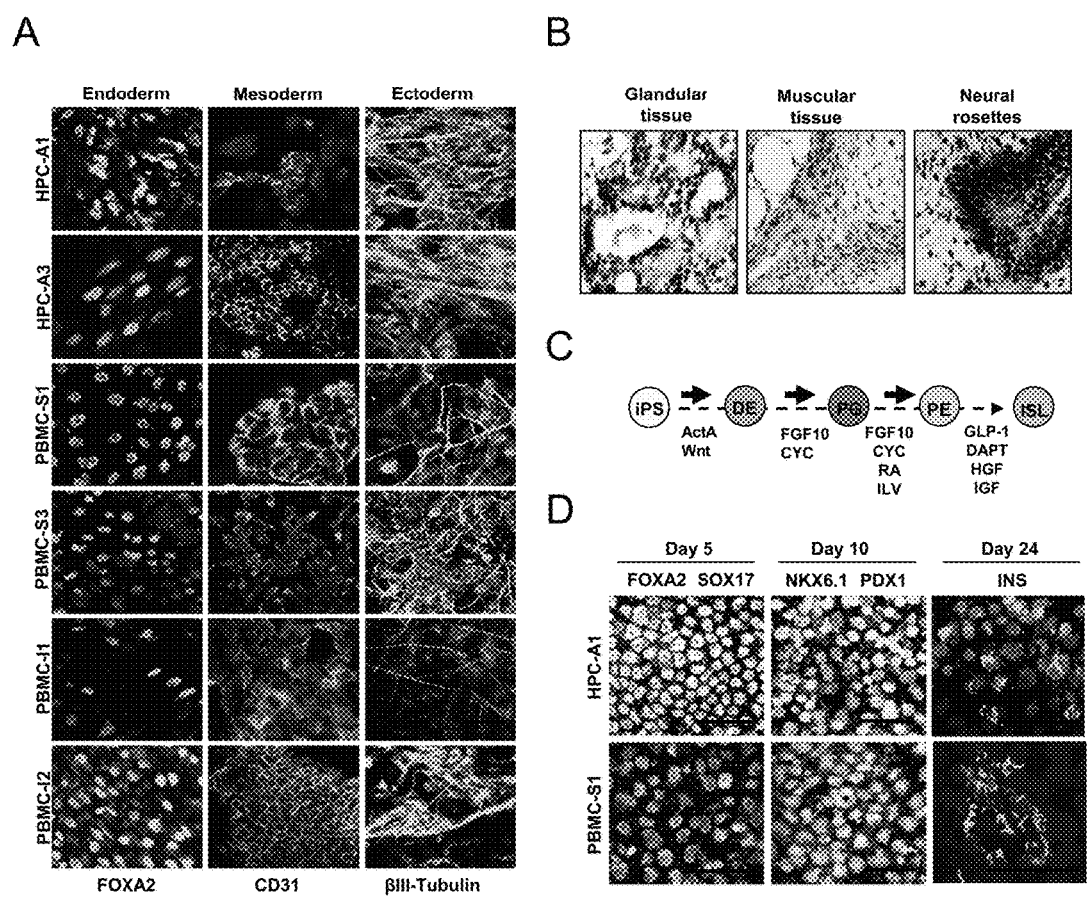

FIG. 15. Differentiation of blood-derived iPSCs in vitro and in vivo. (A) Blood-derived iPSC clones were spontaneously differentiated through embryoid body formation, and analyzed via immunocytochemistry for lineage markers for three embryonic germ layers (endoderm FOXA2, mesoderm CD31 and ectoderm beta-III-tubulin). (B) Transplantation of iPSCs into renal capsule of SCID-beige mice resulted in teratoma formation. Tissue histology of teratomas demonstrated the cells of three germ layers including glandular-, muscular-, and neural rosette-like tissues. (C) Schematic diagram describing the stepwise guided differentiation protocol for iPSC differentiation into islet-like cells. DE, definitive endoderm; PG, primitive gut; PE, pancreatic endoderm; ISL, islet-like cells; ActA, Actinin A; Wnt, Wnt3a; FGF10, fibroblast growth factor 10; CYC, cyclopamine; RA, all trans retinoic acid; ILV, indolactam V; GLP-1, glucagon-like peptide-1; HGF1, hepatocyte growth factor-1 and IGF, insulin-like growth factor-1. (D) Through the guided differentiation protocol, HSC- or PBMC-derived iPSC clones were induced to definitive endoderm (day 5), pancreatic endoderm (day 10) and insulin-producing islet-like cells (day 24). Immunostaining demonstrated the expression of stage-specific markers in iPSC progeny at day 5 (FOXA2 and SOX17), day 10 (NKX6.1 and PDX1) and day 24 (INS). Scale bars indicate 50 µm.

FIG. 16. Expression of pluripotency-associated markers in HK-derived iPS clones. (A) Early-passage HK cells (left panel) were infected with lentivirus (LV) vector encoding OCT4, SOX2, KLF4, and c-MYC. Seven days post-infection (center panel), early iPS-like colonies were detected (right panel in higher magnification). (B) HK-derived iPS clones were either derived from patients who were non-diabetic (ND) or type 2 diabetic (T2D). iPS clones, cultured under feeder-free conditions, exhibited human ES-like morphologies, while expressing high levels of alkaline phosphatase (AP). (C) Patient HK-derived iPS clones were further characterized through immunocytochemistry analysis using a panel of pluripotency markers. All clones were negative for SSEA-1 expression, while staining positive for pluripotency markers SSEA-4, TRA-1-60, TRA-1-81, OCT4, SOX2, KLF4, and NANOG. Scale bars represent 100 µm.

Figure 17:
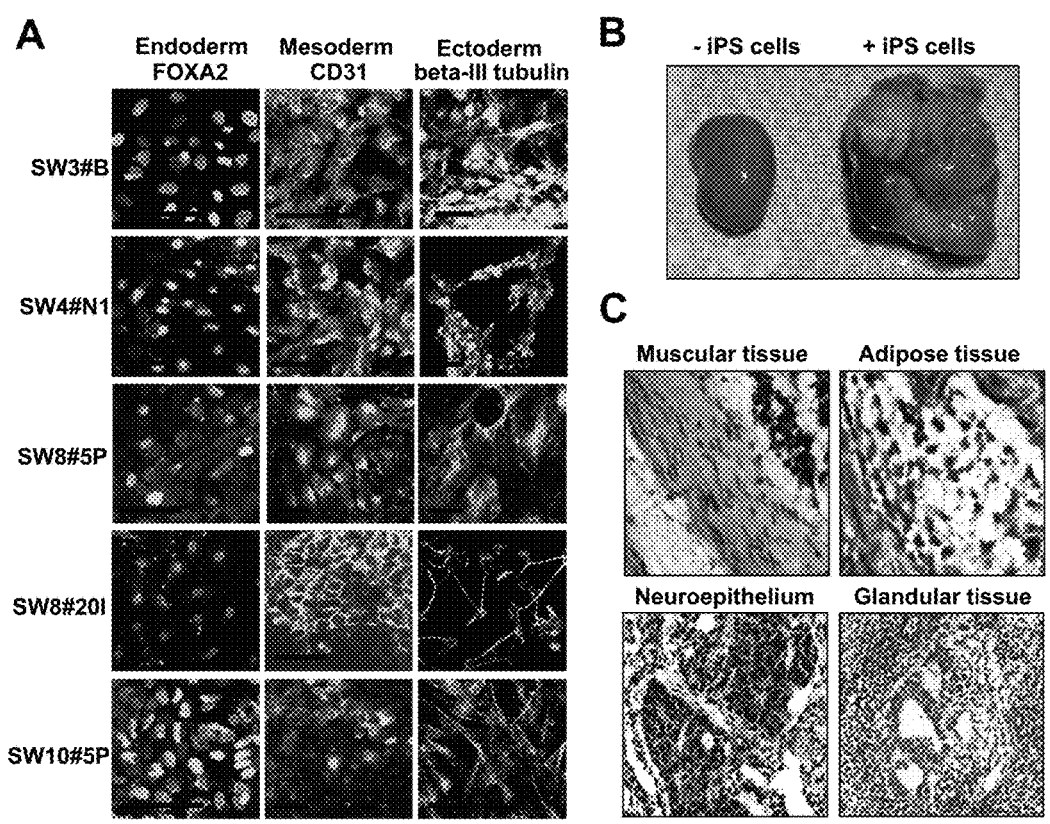

FIG. 17. Pluripotency of HK-derived iPS cells verified through spontaneous differentiation in vitro and in vivo. (A) HK-derived iPS clones were analyzed via immunocytochemistry for lineage markers for three germ layers (endoderm, mesoderm and ectoderm). Scale bars indicate 50 µm. (B) Transplant of HK-derived iPS cells into the kidney capsule of SCID-beige mice resulted in teratoma formation. Pictures of harvested kidneys (with or without iPS transplant) are shown. (C) H&E staining demonstrated multiple lineages within the complex architecture of the tumor, including muscle, adipose, immature neuroepithelium, and glandular tissues.

Figure 18:
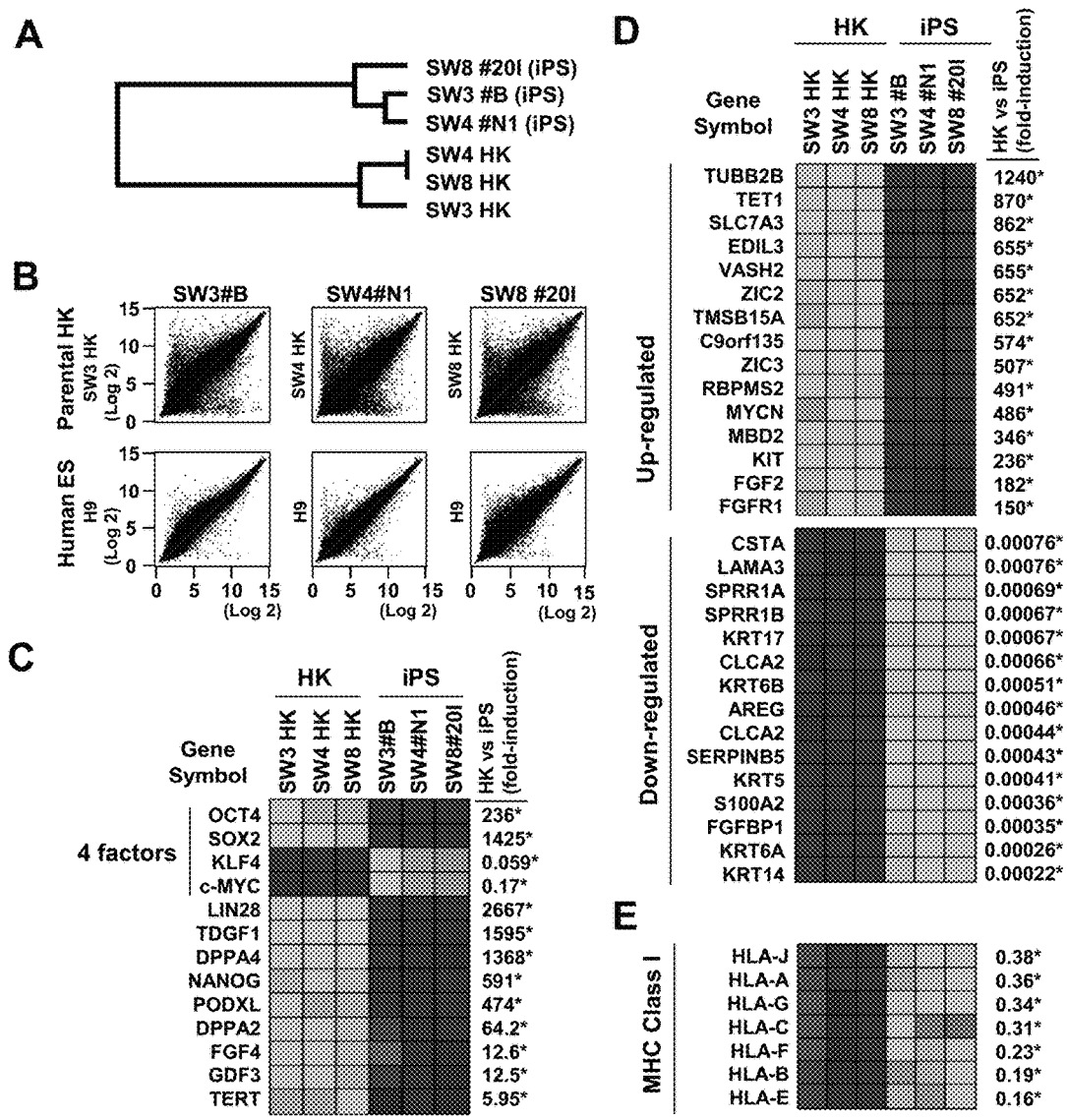

FIG. 18. Variations in gene expression profile upon induced pluripotency. (A) Dendrogram describing the unsupervised hierarchal clustering of patient-derived HK cells and HK-derived iPS cells. (B) Global gene expression patterns of HK-derived iPS clones were compared with their parental HK cells (upper panels), or with that of human embryonic stem cells (H9, lower panels, GSM190779), upon RNA microarray analysis. (C) Heatmap showing the up-regulation and down-regulation (high—black; low—white) of pluripotency-associated genes in HK- and HK-derived iPS clones. The four factors used to induce pluripotency are indicated. The changes in gene expression levels in iPS cells, relative to those in parental HK cells, were calculated using microarray data from three parental HK cells and three HK-derived iPS cells, and shown as fold-induction in iPS cells. Statistically significant changes are indicated by asterisks ($p<0.05$). HK cells originally expressed high levels of endogenous KLF4 and c-MYC, resulting in down-regulation of these two key reprogramming factors in derived iPS cells. (D) Heatmap showing the top 15 genes which were up-regulated (upper panel) or down-regulated (lower panel) upon reprogramming. Statistically significant changes are indicated by asterisks ($p<0.05$). (E) Comparison of the major histocompatibility complex (MHC) class I gene expression profiles between HK and iPS cells. Statistically significant changes are indicated by asterisks ($p<0.05$).

Figure 19:
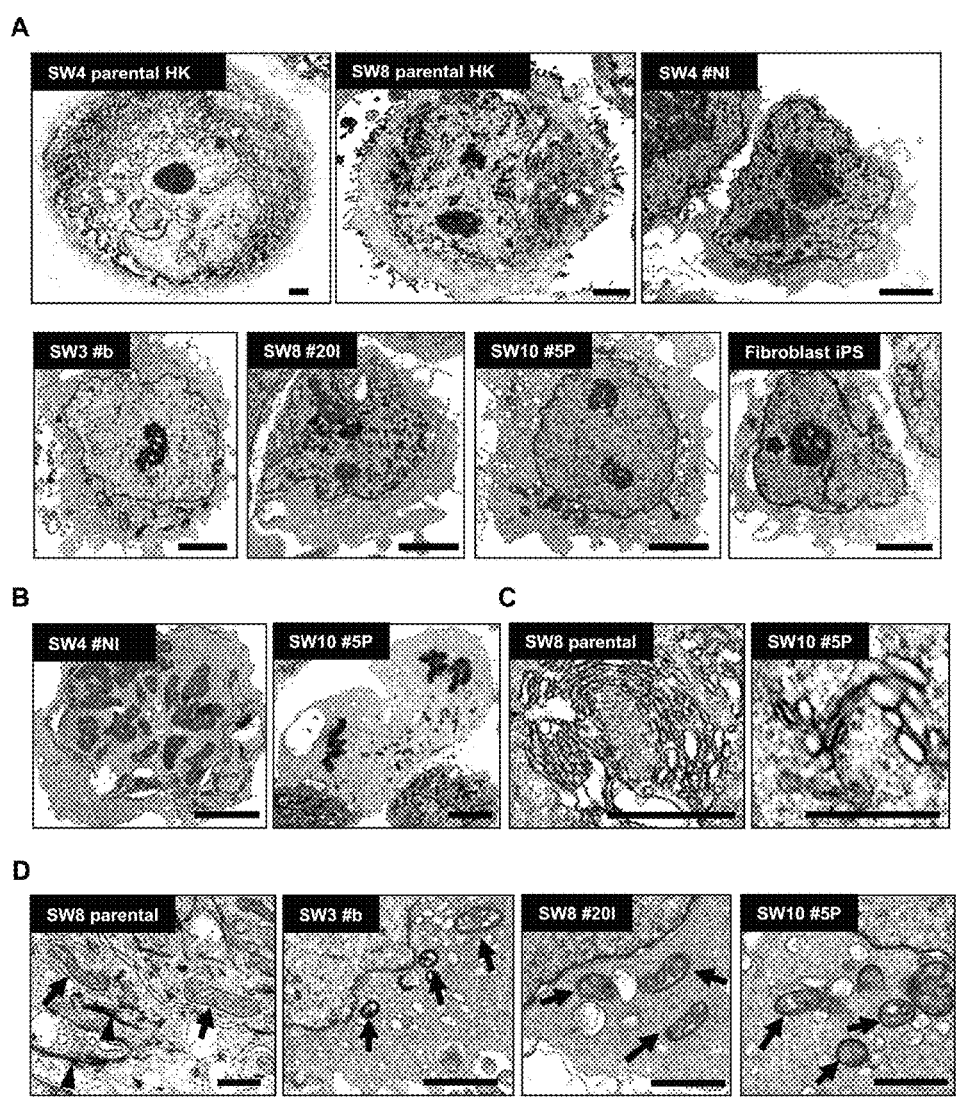

FIG. 19. Morphological variations of patient-derived iPS cells upon reprogramming. (A) High-resolution electron micrographs of HK cells before (SW4 parental HK and SW8 parental HK) and after (SW4 #N1, SW3 #B, SW8 #20I, and SW10 #5P) induced pluripotency. Representative micrograph of a verified fibroblast-derived iPS cell is also included. Scale bars represent 2 µm. (B) Mitotic events of two iPS clones were shown (left panel in metaphase; right panel in anaphase). Scale bars represent 2 µm. (C) Endoplasmic reticulum and the Golgi structures in HK and HK-derived iPS cells are shown. Scale bars represent 0.5 µm. (D) Mature mitochondria with well-developed cristae in parental HK cells (SW8 parental) and immature mitochondria in iPS clones (SW3 #B, SW8 #20I, and SW10 #5P) are indicated by arrows. Keratin intermediate filaments in parental HK cells are indicated by arrowheads. Scale bars represent 0.5 µm.

FIG. 20. Mitochondrial and oxidative-stress response gene expression in induced pluripotency. (A) Relative cytochrome B (CYTB) and NADH mitochondrial DNA (mtDNA) copy numbers before (parental) and after (iPS) reprogramming. mtDNA copy numbers were normalized to total genomic DNA and represented as a percentage of parental cell mtDNA copy number. (B) Immunocytochemistry analysis of iPS clone SW4 #N1 with mitochondrial marker AIF and (C) iPS clones SW4 #N1 and SW10 #5P with MitoTracker (Molecular Probes) staining (D) Heatmap demonstrating up and down-regulation of genes involved in mitochondrial biogenesis upon reprogramming (high—black; low—white). No statistically significant change was observed in any of the genes listed. (E) Heatmap (high—black; low—white) of expression profiles for genes involved in glycolysis, anaerobic glycolysis, and citric acid cycle were compared between parental HK and HK-derived iPS cells. Statistically significant changes are indicated by asterisks ($p<0.05$). (F) RNA expression profiles of genes involved in the mitochondrial/oxidative stress response pathway between parental HK and iPS cells are shown. Statistically significant changes are indicated by asterisks ($p<0.05$).

Figure 21:
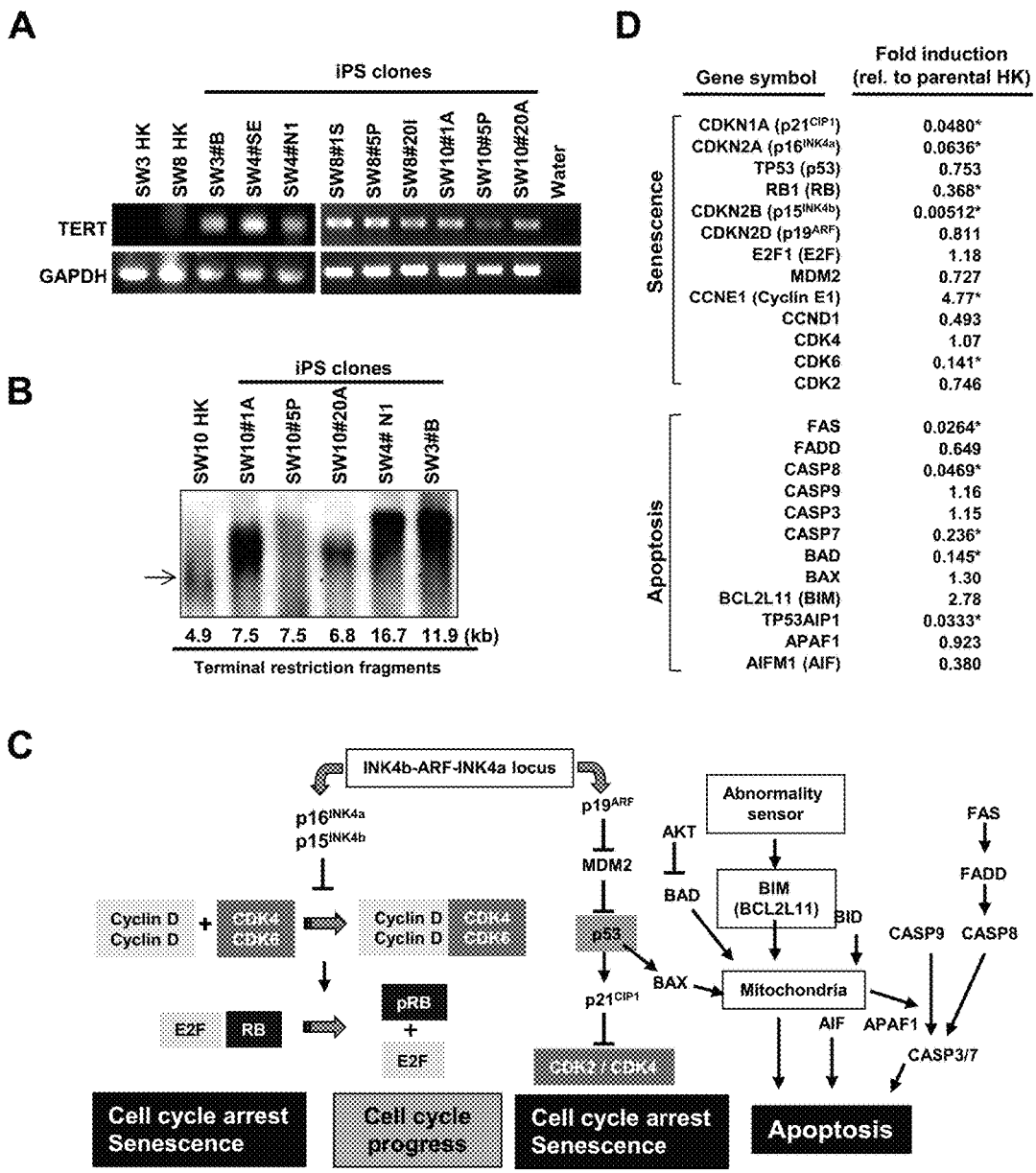

FIG. 21. Comparison of telomerase activity, cellular senescence, and programmed cell death in HK cells before and after induced pluripotency. (A) RT-PCR analysis of TERT-specific transcripts in parental HK cells and iPS clones. GAPDH was used as control. (B) Telomere lengths in HK and HK-derived iPS cells were determined by the terminal restriction fragment lengths. Southern blot analysis and corresponding telomere fragment lengths derived from densitometric quantification are shown. (C) Schematic representation of key senescence- and apoptosis-regulating pathways. (D) Changes in expression levels of key genes, involved in cellular senescence or apoptosis, were determined using the microarray data of three parental HK cells and three HK-derived iPS cells, and fold induction of individual genes in iPS cells, relative to those in parental HK cells, are shown. Statistically significant changes are indicated by asterisks ($p<0.05$).

Figure 22:
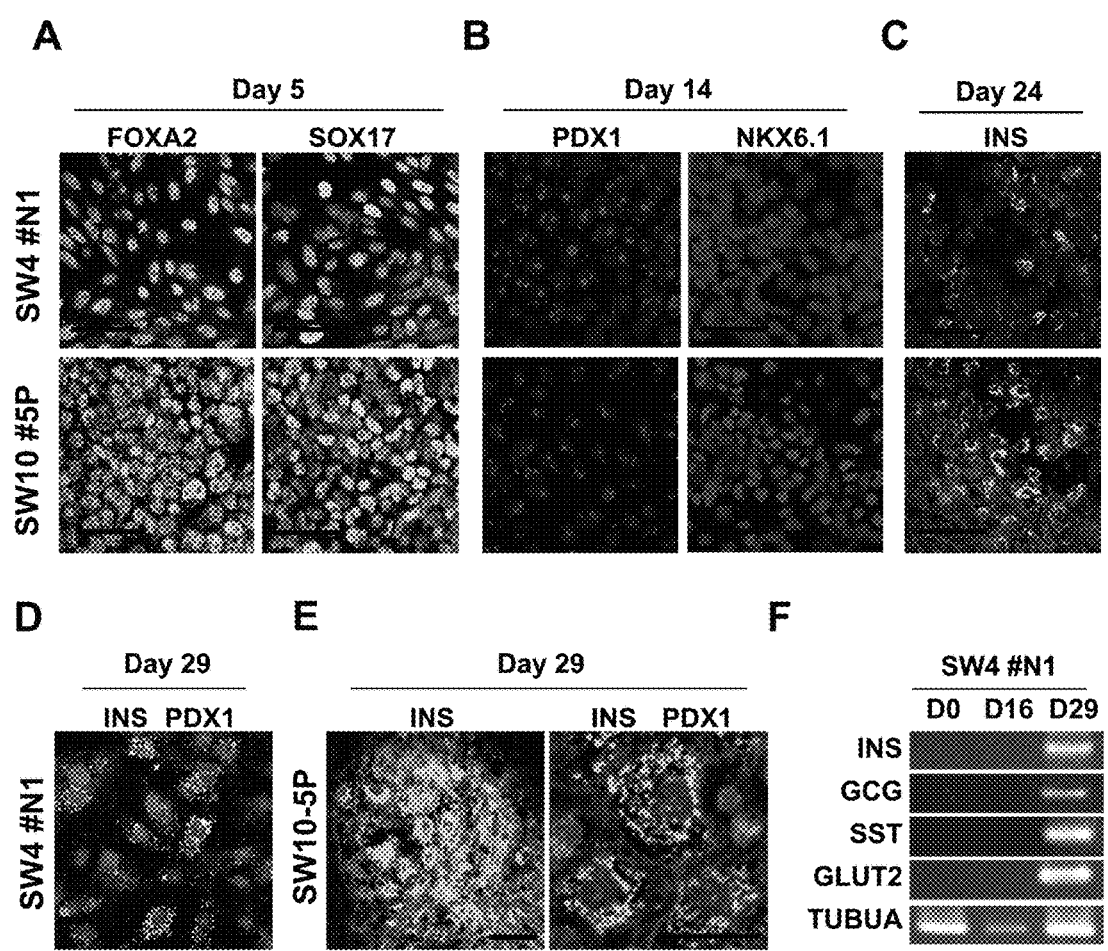

FIG. 22. Guided in vitro differentiation of patient iPS cells into insulin-producing islet-like cells. iPS cells, differentiated through step-wise differentiation, were analyzed by immunocytochemistry for stage-specific markers at day 5 (A), 14 (B), 24 (C) and 29 (D and E). Scale bars indicate 50 µm for A, B, C and E (left panel), and 10 µm for D and E (right panel). (F) RT-PCR analysis of the mRNA of SW4#N1 clone, harvested at differentiation day 0, 16, and 29, confirmed the expression of insulin (INS), glucagon (GCG), somatostatin (SST), and glucose transporter 2 (GLUT2) on day 29. α-tubulin was used as control (TUBUA).

DETAILED DESCRIPTION

This document provides methods and materials related to differentiating iPS cells into glucose-responsive, insulin-secreting progeny. For example, this document provides methods and material for using ILV and GLP-1 to produce glucose-responsive, insulin-secreting progeny from iPS cells.

Any appropriate method can be used to obtain iPS cells. For example, iPS cells can be obtained using polypeptides from a species that is the same species from which the cells (e.g., somatic cells) were obtained. An example of such iPS cells includes human somatic cells that were induced to form iPS cells using human polypeptides. In some cases, iPS cells can be obtained using polypeptides from a species that is different from the species from which the cells (e.g., somatic cells) were obtained. An example of such iPS cells includes human cells that were induced to form iPS cells using mouse polypeptides. Other examples include human cells that were induced to form iPS cells using rat, dog, cow, pig, or monkey (e.g., Rhesus monkey) polypeptides. In some cases, an iPS cell provided herein can be a human cell that was induced to form an iPS cell using non-human polypeptides (e.g., polypeptides of mouse, rat, pig, dog, or monkey origin).

The polypeptides used to induce the formation of iPS cells can include any combination of Oct3/4 polypeptides, Sox family polypeptides (e.g., Sox2 polypeptides), Klf family of polypeptides (e.g., Klf4 polypeptides), Myc family polypeptides (e.g., c-Myc), Nanog polypeptides, and Lin28 polypeptides. For example, nucleic acid vectors designed to express Oct3/4, Sox2, Klf4, and c-Myc polypeptides can be used to obtain iPS cells. In some cases, Oct3/4, Sox2, Klf4, and c-Myc polypeptides can be directly delivered into target cells to obtain iPS cells using a polypeptide transfection method (e.g., liposome or electroporation). In one embodiment, nucleic acid vectors designed to express Oct3/4, Sox2, and Klf4 polypeptides, and not a c-Myc polypeptide, can be used to obtain iPS cells. In some cases, Oct3/4, Sox2, and Klf4 polypeptides can be directly delivered into target cells to obtain iPS cells using a polypeptide transfection method. An Oct3/4 polypeptide can have the amino acid sequence set forth in GenBank® Accession Numbers BC117435 (e.g., GI No. 109659099). An Sox2 polypeptide can have the amino acid sequence set forth in GenBank® Accession Numbers BC013923 (e.g., GI No. 33869633). A Klf4 polypeptide can have the amino acid sequence set forth in GenBank® Accession Numbers BC029923 (e.g., GI No. 20987475). A c-Myc polypeptide can have the amino acid sequence set forth in GenBank® Accession Numbers BC000141 (e.g., GI No. 12652778). A Nanog polypeptide can have the amino acid sequence set forth in GenBank® Accession Numbers BC099704.1 (e.g., GI No. 71043476). A Lin28 polypeptide can have the amino acid sequence set forth in GenBank® Accession Numbers BC028566 (e.g., GI No. 33872076).

Any appropriate cell type can be used to obtain iPS cells. For example, skin, lung, heart, liver, blood, kidney, or muscle cells can be used to obtain iPS cells. Such cells can be obtained from any type of mammal including, without limitation, humans, mice, rats, dogs, cats, cows, pigs, or monkeys. In addition, any stage of the mammal can be used, including mammals at the embryo, neonate, newborn, or adult stage. For example, fibroblasts obtained from an adult human patient can be used to obtain iPS cells. Such iPS cells can be used to treat that same human patient (or to treat a different human) or can be used to create differentiated cells that can be used to treat that same human patient (or a different human). For example, somatic cells from a human patient can be treated as described herein to obtain iPS cells. The obtained iPS cells can be differentiated into glucose-responsive, insulin-producing cells as described herein that can be implanted into that same human patient.

Any appropriate method can be used to introduce nucleic acid (e.g., nucleic acid encoding polypeptides designed to induce iPS cell formation from somatic cells) into a cell. For example, nucleic acid encoding polypeptides (e.g., Oct3/4, Sox2, Klf4, and c-Myc polypeptides) designed to induce the formation of iPS cells from other cells (e.g., non-embryonic stem cells or somatic cells) can be transferred to the cells using recombinant viruses that can infect cells, or liposomes or other non-viral methods such as electroporation, microinjection, transposons, phage integrases, or calcium phosphate precipitation, that are capable of delivering nucleic acids to cells. The exogenous nucleic acid that is delivered typically is part of a vector in which a regulatory element such as a promoter is operably linked to the nucleic acid of interest. The promoter can be constitutive or inducible. Non-limiting examples of constitutive promoters include cytomegalovirus (CMV) promoter and the Rous sarcoma virus promoter. As used herein, "inducible" refers to both up-regulation and down regulation. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, or a physiological stress imposed directly by, for example heat, or indirectly through the action of a pathogen or disease agent such as a virus.

Additional regulatory elements that may be useful in vectors, include, but are not limited to, polyadenylation sequences, translation control sequences (e.g., an internal ribosome entry segment, IRES), enhancers, or introns. Such elements may not be necessary, although they can increase expression by affecting transcription, stability of the mRNA, translational efficiency, or the like. Such elements can be included in a nucleic acid construct as desired to obtain optimal expression of the nucleic acids in the cells. Sufficient expression, however, can sometimes be obtained without such additional elements.

Vectors also can include other elements. For example, a vector can include a nucleic acid that encodes a signal peptide such that the encoded polypeptide is directed to a particular cellular location (e.g., the cell surface) or a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

Any appropriate viral vectors can be used to introduce sternness-related factors such as Oct3/4, Klf4, Sox2 and c-Myc. Examples of viral vectors include, without limitation, vectors based on DNA or RNA viruses such as adenovirus, adeno-associated virus (AAV), retroviruses, lentiviruses, vaccinia virus, measles viruses, herpes viruses, baculoviruses, and papilloma virus vectors. See, Kay et al., Proc. Natl. Acad. Sci. USA, 94:12744-12746 (1997) for a review of viral and non-viral vectors. Viral vectors can be modified so the native tropism and pathogenicity of the virus has been altered or removed. The genome of a virus also can be modified to increase its infectivity and to accommodate packaging of the nucleic acid encoding the polypeptide of interest. In some cases, iPS cells can be obtained using viral vectors that do not integrate into the genome of the cells. Such viral vectors include, without limitation, adenoviral vectors, AAV vectors, baculovirus vectors, and herpesvirus vectors. For example, cells obtained from a human can be provided nucleic acid encoding human Oct3/4, Sox2, Klf4, and c-Myc polypeptides using viral vectors that do not integrate the exogenous nucleic acid into the cells. Once the polypeptides are expressed and iPS cells are obtained, the iPS cells can be maintained in culture such that the iPS cells are devoid of the exogenous nucleic acid.

Any appropriate non-viral vectors can be used to introduce stemness-related factors such as Oct3/4, Klf4, Sox2, and c-Myc. Examples of non-viral vectors include, without limitation, vectors based on plasmid DNA or RNA, retroelement, transposon, and episomal vectors. Non-viral vectors can be delivered to cells via liposomes, which are artificial membrane vesicles. The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Transduction efficiency of liposomes can be increased by using dioleoylphosphatidylethanolamine during transduction. See, Felgner et al., J. Biol. Chem., 269:2550-2561 (1994). High efficiency liposomes are commercially available. See, for example, Super-Fect® from Qiagen (Valencia, Calif.).

In some cases, iPS cells can be obtained using culture conditions that do not involve the use of serum, feeder cells, or serum and feeder cells. For example, cells obtained from a human can be provided nucleic acid encoding human Oct3/4, Sox2, Klf4, and c-Myc polypeptides and cultured using media lacking serum (e.g., human or non-human serum) and lacking feeder cells (e.g., human or non-human feeder cells).

Once obtained, iPS cells can be exposed to ILV and GLP-1. For example, human iPS cells can be cultured in the presence of retinoic acid (e.g., all-trans retinoic acid; RA), an FGF10 polypeptide, KAAD-cyclopamine (CYC), and ILV for a period of time (e.g., about 5 to 15 days, about 6 to 15 days, about 5 to 13 days, about 6 to 13 days, about 7 to 12 days, or about 8 to 11 days). After at least about 8 days, the resulting cells can be cultured in the presence of an hepatocyte growth factor (HGF) polypeptide, an insulin like growth factor (IGF) polypeptide, N-[N-(3,5-Difluorophenacetyl)-L-alanyl]-S-phenylglycine t-butyl ester (DAPT), and GLP-1 for a period of time (e.g., about 10 to 30 days, about 12 to 30 days, about 14 to 30 days, about 10 to 25 days, about 14 to 25 days, or about 15 to 24 days) sufficient to result in a population of glucose-responsive, insulin-secreting cells. In some cases, iPS cells (e.g., human iPS cells) can be cultured in the presence of RA, FGF10, CYC, ILV, HGF, IGF, DAPT, and GLP-1 for a period of time (e.g., about 10 to 30 days, about 12 to 30 days, about 14 to 30 days, about 10 to 25 days, about 14 to 25 days, or about 15 to 24 days) sufficient to result in a population of glucose-responsive, insulin-secreting cells.

An FGF10 polypeptide can have the amino acid sequence set forth in GenBank® GI No. 255090638. An HGF polypeptide can have the amino acid sequence set forth in GenBank® GI No. 188595715. A IGF polypeptide can have the amino acid sequence set forth in GenBank® GI No. 163659904. A GLP-1 polypeptide can have the amino acid sequence set forth in GenBank® Accession Numbers NM 002054.3 (e.g., GI No. 291190799).

Any appropriate amount of these agents (or combination of agents) can be used to obtain glucose-responsive, insulin-secreting cells from iPS cells. For example, between about $\mu$M and about 3 $\mu$M (e.g., about 2 $\mu$M) of RA, between about 25 ng/mL and about 75 ng/mL (e.g., about 50 ng/mL) of FGF10 polypeptide, between about 0.2 $\mu$M and about 0.3 $\mu$M (e.g., about 0.25 $\mu$M) of CYC, between about 200 nM and about 400 nM (e.g., about 300 nM) of ILV, between about 25 ng/mL and about 75 ng/mL (e.g., about 50 ng/mL) of HGF polypeptide, between about 25 ng/mL and about 75 ng/mL (e.g., about 50 ng/mL) of IGF polypeptide, between about 5 $\mu$M and about 15 $\mu$M (e.g., about 10 $\mu$M) of DAPT, between about 25 nM and about 75 nM (e.g., about 55 nM) of GLP-1 polypeptide can be used together or in various combinations with culture medium to obtain glucose-responsive, insulin-secreting cells from iPS cells.

Any appropriate method can be used to determine whether or not cells formed from iPS cells are glucose-responsive, insulin-secreting cells. For example, a C-peptide release assay can be performed to confirm the formation of glucose-responsive, insulin-secreting cells.

Once obtained, the glucose-responsive, insulin-secreting cells can be administered to a patient to treat, for example, diabetes (e.g., type 1 diabetes). For example, iPS-derived pancreatic endoderm cells or glucose-responsive islet-like cells can be transplanted into a human under a renal capsule, liver, fat pad, or subcutaneously.

The invention will be further described in the following examples, which do not limit the scope of the invention described in the claims.

EXAMPLES

Example 1

ILV/GLP-1-Mediated Differentiation of Human iPS Cells into Glucose-Responsive Insulin-Secreting Progeny Plasmid Construction and Lentiviral Vector Production Sternness factor-expressing lentiviral pSIN-CSGWd1NotI-derived transfer vectors were generated as described elsewhere (Nelson et al., Circulation, 120:408-416 (2009)). In brief, the packaging plasmid pEX-QV was engineered with H87Q mutation in the HIV-1 capsid region for increased transduction efficiency of purified infectious supernatants (Nelson et al., Clin. Transl. Sci., 2:118-126 (2009)). HIV vectors were produced by transient transfection of 293T cells and titrated by immunostaining (Nelson et al., Clin. Transl. Sci., 2:118-126 (2009)). Vectors expressed pluripotency factors from a spleen focus-forming virus (SFFV) promoter (Nelson et al., Clin. Transl. Sci., 2:118-126 (2009)).

Generation and Culture of Human iPS Cells on SNL Feeder Cells

Human neonatal foreskin fibroblasts (BJ1) (ATCC#CRL-2522) and primary human cardiac fibroblasts (HCF) (SciencCell #6300) were seeded one day before infection in wells of 6 well plates with DMEM containing 10% FBS, Penicillin (100 U/mL) and Streptomycin (100 µg/mL) (Pen/Strep) (complete DMEM). Fibroblasts were infected with lentiviral vectors expressing OCT4, SOX2, KLF4, and c-MYC at a multiplicity of infection about 5 each. After 12 hours of viral infection, cells were fed with fresh complete DMEM. Vector-transduced cells were replated 4 days after infection at $5 \times 10^4$ cells per 100 mm dish on mitomycin-C treated SNL feeder cells in complete DMEM. Next day, the medium was replaced with the serum-free HEScGRO medium (Millipore #SCMO20) supplemented with basic fibroblast growth factor (bFGF, 20 ng/mL; Peprotech). Cells were fed with fresh HEScGRO medium every two days. Putative iPS colonies, which began to appear 3-4 weeks after vector transduction, were picked based on size and human embryonic stem cell-like colony morphology, and expanded through dissociation with the cell dissociation buffer (Invitrogen #13151014). BJ1-derived iPS clones, BJ#SA and BJ#SD, were generated on SNL feeder cells. Established iPS clones were maintained in feeder-free condition.

Feeder-Free iPS Generation and Culture

For feeder cell-free iPS generation and maintenance on Matrigel (BD Biosciences #354277)-coated plates, various commercially available stem cell media or their combinations were compared. Optimal results were obtained when iPS cells were maintained in a feeder cell-free medium, which contained HEScGRO with 25% of mTeSR1 medium (Stemcell Technologies #05850) and 20 ng/mL of bFGF (iPS medium). In order to generate feeder-cell free iPS clones from BJ and HCF fibroblasts, cells were transduced with pluripotency factor-expressing lentiviral vectors, 4 days after infection. The cells were re-plated at a density of 5 x $10^5$ cells on a Matrigel-coated 100 mm dish. Medium was replaced with fresh iPS medium every two days. Putative iPS colonies were observed 1-2 weeks after vector transduction. iPS clones were picked based on morphology and size. iPS clones were expanded with cell dissociation buffer and passaged at a 1:2-1:8 split ratio every 3-7 days depending on cell density. BJ#1, HCF#1, and HCF#6 iPS clones were generated and maintained under feeder cell-free conditions.

RT-PCR

RT-PCR analyses were performed using the primers indicated in Table 1.

TABLE 1

RT-PCR primer sequences for human genes analyzed for characterization of human iPS cells and differentiation into insulin-producing cells.

| Gene | Forward Sequence | SEQ ID NO: | Reverse Sequence | SEQ ID NO: | Accession Number | GI No.: |
|---|---|---|---|---|---|---|
| OCT4 | AGCGAACCAGTATCGAGAAC | 1 | TTACAGAACCACACTCGGAC | 2 | BC117435.1 | 109659099 |
| SOX2 | AGCTACAGCATGATGCAGGA | 3 | GGTCATGGAGTTGTACTGCA | 4 | BC013923.2 | 33869633 |
| NANOG | TGAACCTCAGCTACAAACAG | 5 | TGGTGGTAGGAAGAGTAAAG | 6 | AB093576.1 | 31338865 |
| MYC | ACTCTGAGGAGGAACAAGAA | 7 | TGGAGACGTGGCACCTCTT | 8 | BC000141 | 12652778 |
| KLF4 | TCTCAAGGCACACCTGCGAA | 9 | TAGTGCCTGGTCAGTTCATC | 10 | BC029923.1 | 20987475 |
| hTERT | TGTGCACCAACATCTACAAG | 11 | GCGTTCTTGGCTTTCAGGAT | 12 | AB085628.1 | 22759945 |
| GDF3 | AAATGTTTGTGTTGCGGTCA | 13 | TCTGGCACAGGTGTCTTCAG | 14 | AF263538.1 | 9652071 |
| FOXA2 | CTACGCCAACATGAACTCCA | 15 | AAGGGGAAGAGGTCCATGAT | 16 | AB028021.1 | 4958949 |
| PDX1 | CCCATGGATGAAGTCTACC | 17 | GTCCTCCTCCTTTTTCCAC | 18 | U30329.1 | 929922 |
| NEUROG3 | GTAGAAAGGATGACGCCTCAACC | 19 | TCAGTGCCAACTCGCTCTTAGG | 20 | BC069098.1 | 46575675 |
| ISL-1 | ATTTCCCTATGTGTTGGTTGCG | 21 | CGTTCTTGCTGAAGCCGATG | 22 | U07559.1 | 533418 |
| NEUROD1 | GAACGCAGAGGAGGACTCAC | 23 | GTGGAAGACATGGGAGCTGT | 24 | BT019731.1 | 54696327 |
| NKX6.1 | ACACGAGACCCACTTTTTCCG | 25 | TGCTGGACTTGTGCTTCTTCAAC | 26 | NM_006168.2 | 111120317 |
| GLUT2 | GCTACCGACAGCCTATTCTA | 27 | CAAGTCCCACTGACATGAAG | 28 | NM_000340.1 | 4557850 |
| MaFA | CTTCAGCAAGGAGGAGGTCATC | 29 | CTCGTATTTCTCCTTGTACAGGTCC | 30 | NM_201589.2 | 71274110 |
| INS | AGCCTTTGTGAACCAACACC | 31 | GCTGGTAGAGGGAGCAGATG | 32 | NM_000207.2 | 109148525 |
| GCG | AGGCAGACCCACTCAGTGA | 33 | AACAATGGCGACCTCTTCTG | 34 | BT006813.1 | 30582464 |
| SST | GTACTTCTTGGCAGAGCTGCTG | 35 | CAGAAGAAATTCTTGCAGCCAG | 36 | BC032625.1 | 21619155 |
| GAPDH | AGCCACATCGCTCAGACACC | 37 | GTACTCAGCGGCCAGCATCG | 38 | BT006893.1 | 30582624 |

Immunostaining and Alkaline Phosphatase Staining

For immunostaining, iPS cells were fixed for 20 minutes at room temperature (RT) in 4% paraformaldehyde (PFA) in PBS, washed in PBS, and blocked for 30 minutes with 5% FBS in PBST (PBS with 0.1% Tween-20 (Sigma). Cells were stained with primary antibodies overnight at 4° C., rinsed by PBS, and incubated with secondary antibodies 1 hour at RT (Martinez-Fernandez et al., Circ. Res., 105:648-656 (2009)). Cells at different stages of differentiation were fixed and stained with primary and secondary antibodies. Primary and secondary antibodies used for characterization of iPS and derived cells were: SSEA-1, SSEA-4, TRA-1-60, TRA-1-81 (Millipore #SCR001), OCT4 (Cell Signaling Technology #2750), SOX2 (Cell Signaling Technology #2748), KLF4 (Abcam #ab26648), NANOG (Abcam #ab21624), mouse anti-SOX17 (R&D Systems #MAB1924), rabbit anti-HNF3 beta/FOXA2 (Millipore #07-633), rabbit anti-PDX1 (Santa Cruz Biotechnology #sc-25403), rabbit anti-NGN3 (Millipore #AB5684), rabbit anti-NEUROD1 (Abcam #16508), mouse anti-insulin (Sigma #I2018), rabbit anti-C-peptide (Cell Signaling Technology #4593), rabbit anti-Insulin (Cell Signaling Technology #4590), mouse anti-proinsulin C-peptide (Millipore #CBL94), mouse anti-glucagon (Abcam #ab10988), MafA (Santa Cruz Biotechnology #sc-66958), and rabbit anti-somatostatin (Dako #A0566). Texas Red-conjugated donkey-anti-rabbit IgG (Jackson Laboratories #711-075-152), Texas Red conjugated donkey-anti-mouse IgG (Jackson Laboratories #715-075-151), FITC conjugated donkey-anti-rabbit IgG (Jackson Laboratories #711-095-152), and FITC conjugated donkey-anti-mouse IgG (Jackson Laboratories #715-095-151) were used as secondary antibodies. DAPI was used for counterstaining Stained cells were analyzed using confocal laser-scanning microscopy (Zeiss, LSM 510 confocal scanning laser system). Alkaline phosphatase staining was performed with an Alkaline Phosphatase Detection Kit (Millipore) as described elsewhere (Martinez-Fernandez et al., *Circ. Res.*, 105:648-656 (2009)).

Spontaneous Differentiation

For spontaneous differentiation, iPS clones were dissociated using collagenase IV and plated on low adhesion plates in basal HEScGRO medium (SCM 021) without bFGF. Embryoid bodies (EBs) were cultured as suspension for 7-14 days and were adherent in knockout DMEM with 20% FBS for an additional 7-14 days. For immunofluorescence analysis, cells were fixed and stained (Martinez-Fernandez et al., *Circ. Res.*, 105:648-656 (2009)). Primary antibodies were: FOXA2 for endoderm, beta III tubulin (Abcam #41489) for ectoderm and CD31 (Santa Cruz Biotechnology #SC1506) for mesoderm, while Texas Red-conjugated donkey-anti-rabbit IgG (Jackson Laboratories #711-075-152) and FITC-conjugated donkey-anti-chicken IgG (Jackson Laboratories #703-095-155) were used as secondary antibodies.

Teratoma Formation and Analysis

A teratoma formation assay was performed using an approved protocol. iPS cells were injected subcutaneously into the flank skin of 2-3 months old athymic nude mice at 500,000 cells/50 µL medium. Tumor growth was observed 4-6 weeks after injection. Tumors were processed by rapid freezing, cut as cryosections, and stained with hematoxylin and eosin dyes (Nelson et al., *Clin. Transl. Sci.*, 2:118-126 (2009)).

In Vitro Differentiation of Human iPS Cells to Insulin-Secreting Islet-like Clusters At the first step of differentiation, human iPS clones were treated with 25 ng/mL Wnt3a (R&D systems) and 100 ng/mL activin A (Peprotech) in advanced RPMI (A-RPMI, Invitrogen) with Pen/Strep for 1 day, followed by treatment with 100 ng/mL activin A in A-RPMI supplemented with 0.2% FBS (Invitrogen) for two days. At step two, cells were cultured in A-RPMI medium containing 50 ng/mL FGF10 (R&D systems), 0.25 µM KAAD-cyclopamine (CYC), and 2% FBS for 2 days. Cells were then treated with 50 ng/mL FGF10, 0.25 µM CYC, and 2 µM all-trans Retinoic Acid (RA) (Sigma) in DMEM (Invitrogen) supplemented with Pen/Strep, 1× B27 supplement (Invitrogen) for 4 days at step three. Cells were then cultured in the presence of 50 ng/mL FGF10, 300 nM ILV (Axxora), and 55 nM GLP-1 (Sigma) in DMEM with 1 × B27 for 4 days at step four. In step five, differentiation medium included 10 µM DAPT (Sigma) and 55 nM GLP-1 in DMEM with 1× B27 and culture lasted 6 days. Finally, in step six, cells were cultured in the presence of 50 ng/mL hepatocyte growth factor (HGF) (R&D systems), 50 ng/mL Insulin-like growth factor 1 (IGF-1) (R&D systems) and 55 nM GLP-1 in CMRL-1066 medium (Invitrogen) with 1× B27 for 6 days. All experiments were repeated more than three times.

C-peptide Content and Glucose Stimulated Secretion Assays

A C-peptide release assay was performed by incubating derived islet-like clusters in Krebs-Ringer solution with bicarbonate and HEPES (KRBH; 129 mM NaCl, 4.8 mM KCl, 2.5 mM $CaCl_2$, 1.2 mM $KH_2PO_4$, 1.2 mM $MgSO_4$, 5 mM $NaHCO_3$, 10 mM HEPES, and 0.1% (wt/vol) BSA). Initial incubation was performed in KRBH buffer containing 2.5 mM D-glucose for 1 hour at 37° C., followed by incubation in glucose stimulation conditions containing 10 mM D-glucose and 27.7 mM D-glucose for 1 hour at 37° C. C-peptide or proinsulin levels were determined using an ultrasensitive C-peptide/proinsulin ELISA kit (Alpco Diagnostics).

Flow Cytometry

Single-cell suspensions of differentiating human iPS cells were obtained by dissociating cells with TrypLE (Invitrogen #12605) at 37° C. Intracellular antibody staining was performed using BD Cytofix/Cytoperm and BD Perm/Wash buffer. The following antibodies were used: mouse-anti-SOX17 (R&D Systems #MAB1924), guinea pig-anti-insulin (Dako Cytomation #A0564), goat-anti-mouse Alexa Fluor 488 (Invitrogen #A11029), and donkey-anti-guinea pig-Cy5 (Jackson ImmunoResearch Laboratories #706-176-148). Flow cytometry data were acquired on a Becton Dickinson FACS Calibur and analyzed using Flowjo software.

Results

Reprogramming of Human Fibroblasts with Stemness Factors

Figure 1:
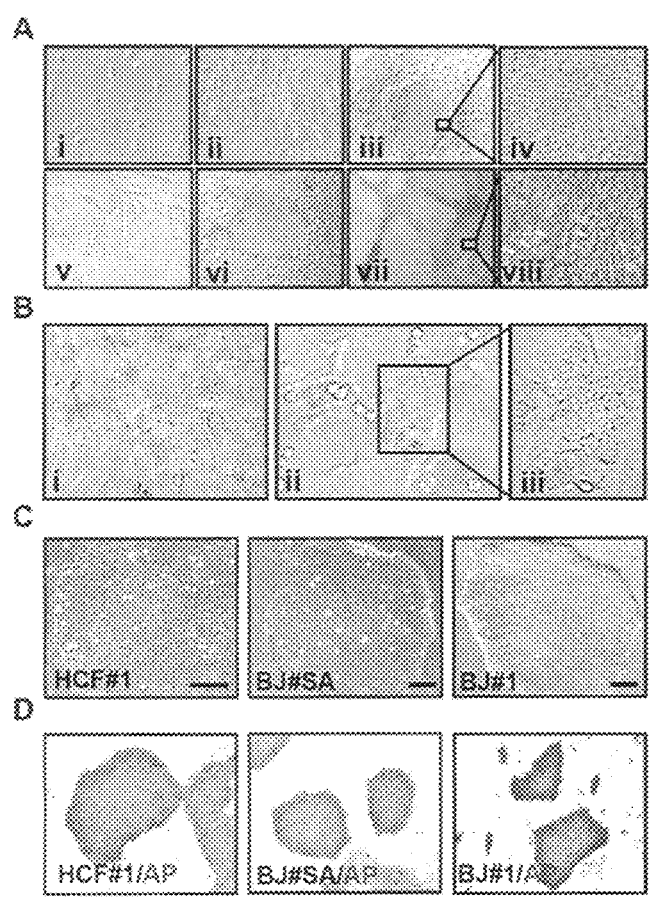
FIG. 1. Generation of Human iPS Clones from BJ and HCF Fibroblasts. (A) Lentiviral vector-mediated delivery of OCT3/4, SOX2, KLF4, and c-MYC resulted in iPS-like colony formation. (i) SNL feeder cells, (ii) uninfected HCF fibroblasts, (iii) HCF-derived iPS-like colony at two weeks post-infection, (iv) iPS-like cells with high magnification. iPS cells exhibited morphology similar to human ES cells, characterized by large nuclei and scant cytoplasm, (v) uninfected BJ fibroblasts, (vi) BJ fibroblasts-derived iPS-like colony at two weeks after infection, (vii) image of a BJ-derived clone expanded on feeder cells, (viii) high magnification image of BJ-derived clone. (B) Feeder-free generation of human iPS cells allowed visualization of the early reprogramming events. (i) Uninfected BJ fibroblasts, (ii) an early stage iPS-like colony in vector-transduced BJ cells one week after infection, (iii) high magnification image of BJ fibroblast-derived iPS-like colony. (C) Morphology of iPS clones cultured under feeder-free conditions. BJ#SA was established on SNL feeder cells, while HCF#1 and BJ#1 were derived feeder-free. (D) HCF#1, BJ#SA and BJ#1 cultured under feeder-free conditions expressed high levels of alkaline phosphatase (AP).
Figure 2:
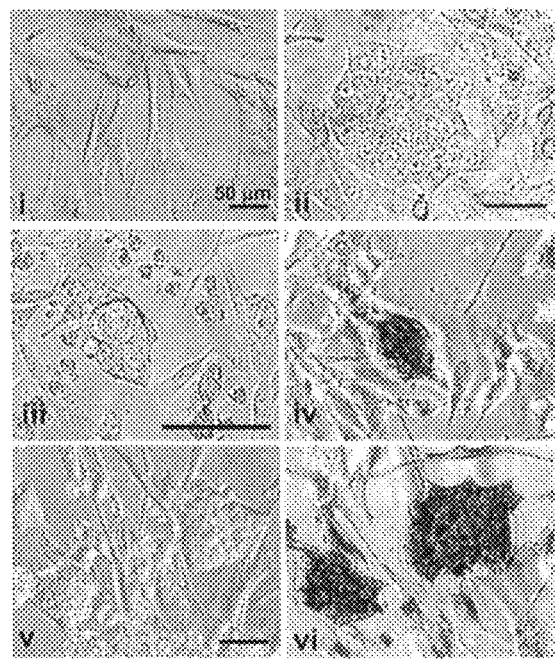
FIG. 2. Feeder-free generation of human iPS cells allowed visualization of the early reprogramming events. For feeder-free iPS generation, BJ and MRCS fibroblasts were infected with lentiviral vectors expressing OCT4, SOX2, KLF4 and c-MYC (4 factor). After four days of infection, cells were replated on Matrigel coated plates. i. Uninfected BJ fibroblasts, ii. BJ fibroblast-derived iPS-like colony at 7 days after infection, iii. BJ fibroblast-derived iPS-like colony at 8 days after infection, iv. The colony shown in (iii) was positive for alkaline phosphatase, v. MRCS-derived iPS-like colonies at 12 days after vector transduction, vi. The same colonies shown in (v) were positive for alkaline phosphatase at 15 days after infection.

HCF and BJ fibroblasts were infected with lentiviral vectors encoding OCT4, SOX2, KLF4, and c-MYC, and transduced cells re-seeded on mitomycin C-inactivated SNL feeder cells or replated on matrigel-coated plates to ensure feeder cell-free culture. On SNL feeder cells, reprogrammed colonies, characterized by distinct morphology of sharp-edged, flat, tightly-packed structures were visible 2 weeks after viral vector transduction (FIG. 1A). Under feeder cell-free conditions, similar colonies were observed as early as day 6 after viral vector infection (FIG. 1B) with clusters of 30-50 cells expressing alkaline phosphatase (FIG. 2). The number of expandable colonies formed on feeders or on non-feeders plates were 5 to 20 clones per $10^5$ transduced cells. Identified colonies were picked at 3 to 6 weeks to allow sufficient growth after viral transduction.

Expression of Pluripotency Markers in Derived iPS Clones

Figure 3:
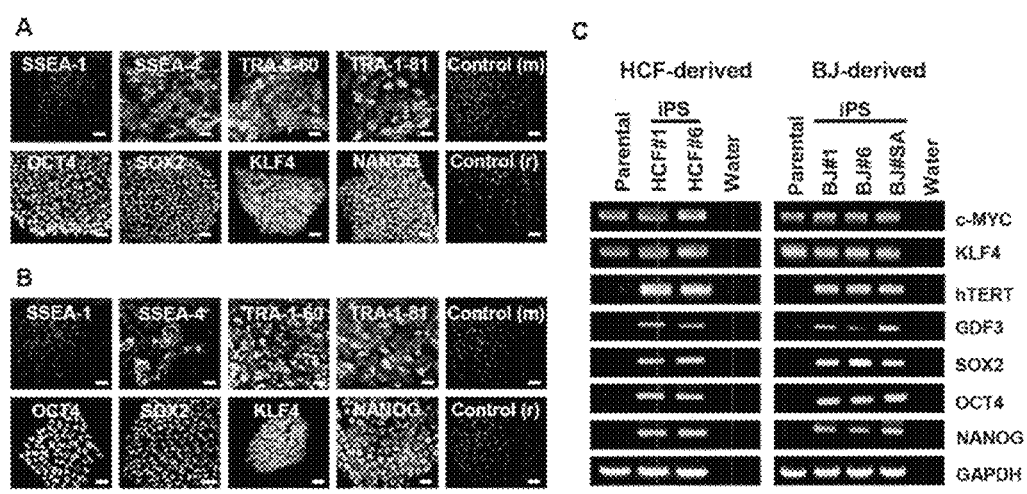
FIG. 3. Expression of Pluripotency-Associated Genes in Putative iPS Clones. (A) and (B) HCF- and BJ-derived iPS clones were analyzed for expression of pluripotency markers by immunostaining HCF#1 and BJ#SA cells were positive for pluripotency markers SSEA4, TRA-1-60, TRA-1-81, OCT4, SOX2, KLF4, and NANOG, while no notable staining was observed for SSEA1. Cells were counterstained with 4', 6-diamidino-2-phenylindole (DAPI). Control (m) and Control (r); control cells treated with FITC-conjugated secondary antibodies against mouse IgG and rabbit IgG. Scale bars indicate 20 μm. (C) HCF- and BJ-derived iPS-like clones were analyzed for pluripotency-associated gene expression by RT-PCR. Total cellular RNA from parental BJ and HCF fibroblasts and no template (water) samples were included as controls. Glyceraldehyde-3-phosphate dehydrogenase (GAPDH) gene transcript was amplified as an internal RNA control.

Over 3-9 months or 30-90 passages, putative iPS clones cultured under feeder cell-free and serum-free conditions exhibited a distinctive morphology similar to that of human ES cells over long-term culture (FIG. 1C). Tested clones expressed high levels of alkaline phosphatase (FIG. 1D). Immunocytochemistry revealed expression of SSEA-4, TRA-1-60, TRA-1-81, OCT4, SOX2, KLF4, and NANOG in multiple clones (FIGS. 3A and 3B). These clones were negative for SSEA-1 expression. RT-PCR of total cellular RNA further demonstrated induction of endogenous pluripotency-associated genes, including OCT4, SOX2, GDF3, telomerase (TERT), KLF4, c-MYC, and NANOG (FIG. 3C). No notable difference was observed between clones isolated from BJ and HCF fibroblasts, or with clones isolated with SNL feeder cells. Morphology and expression of stem cell genes indicated establishment of human iPS clones from fibroblasts, and maintenance in an undifferentiated state under feeder-free conditions.

Pluripotency Validated through Three Germ Layer Differentiation

Figure 4:
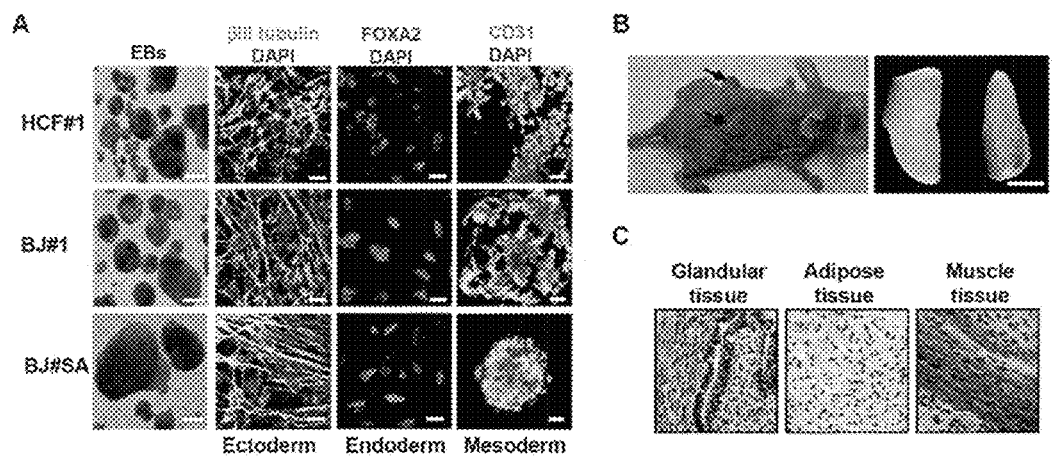
FIG. 4. Spontaneous Differentiation of HCF- and BJ Fibroblast-derived iPS Cells into Cells of Three Embryonic Germ Layers. (A) In vitro differentiation of HCF#1, BJ#1, and BJ#SA clones in suspension culture as embryoid bodies (EB) was followed by monolayer culture for spontaneous differentiation. HCF#1, BJ#1, and BJ#SA clones generated EBs with varying sizes. Cells of ectoderm, endoderm, and mesoderm lineages were confirmed by beta III tubulin (green stain was used), FOXA2 (red stain was used), and CD31 (PECAM-1) (green stain was used), respectively. Cells were counterstained with DAPI. Scale bars on right 50 μm and left 20 μm. (B) Teratoma formation. iPS cells 500,000 were injected subcutaneously into athymic nude mice. Tumor growth was detected only from sites injected with iPS cells. After 3 months tumors were harvested. Scale bar indicates 2 mm. (C) H&E staining of teratoma sections demonstrated multiple lineages within the complex architecture of the tumor, including ectoderm (glandular tissue), endoderm (adipose tissue), and mesoderm (muscular tissue) tissues.

Human iPS clones were assayed, through embryoid body (EB) formation, for the ability to spontaneously differentiate in vitro into cells of the three embryonic germ layers. All iPS clones assayed formed EBs (FIG. 4A). After variable times in suspension, EBs were transferred to adherent conditions and further cultured. Immunostaining for lineage-specific markers confirmed that human iPS cells differentiated into ectoderm (beta-III tubulin, FIG. 4A), endoderm (FOXA2, FIG. 4A) and mesoderm (CD31, FIG. 4A) lineages. Moreover, in vivo human iPS cells formed teratomas after injection into nude mice. These subcutaneous tumors enlarged up to 1 cm in diameter within 3 months post-injection (FIG. 4B). Histology revealed diverse cell types, including glandular epithelium (ectoderm, FIG. 4C), adipose (endoderm, FIG. 4C) and muscular (mesoderm, FIG. 4C) tissues. Thus, human iPS cells generated from BJ and HCF fibroblasts exhibit hallmark properties of pluripotent stem cells.

Differentiation of Human iPS cells into Pancreatic Endoderm

Figure 5:
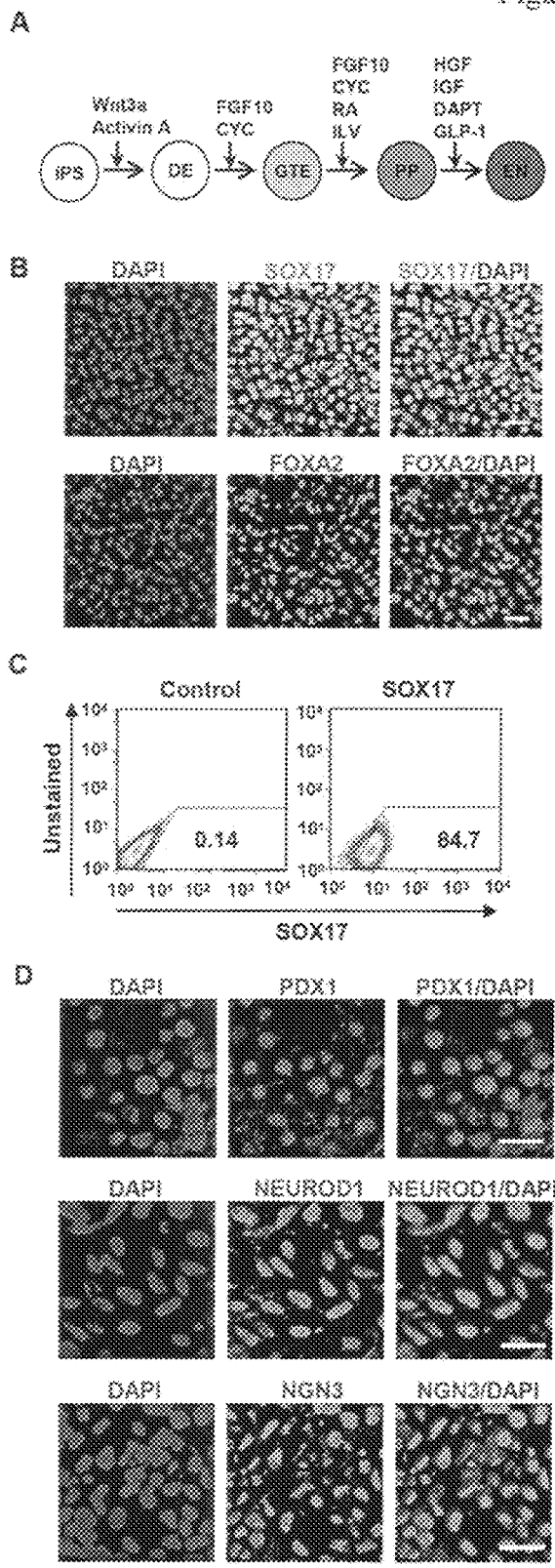
FIG. 5. Differentiation of Human iPS Cells into Pancreatic Endoderm Cells. (A) Schematic representation of the stepwise differentiation protocol for generation of islet-like clusters from human iPS cells. DE, definitive endoderm; GTE, gut tube endoderm; PP, pancreatic progenitor; EN, endocrine hormone expressing cells; CYC, KAAD-cyclopamine; RA, all-trans retinoic acid; ILV, indolactam V; HGF, hepatocyte growth factor; IGF, insulin like growth factor; and GLP-1, glucagon-like peptide-1. (B) Induction of definitive endoderm cells.

Normal differentiation of a pluripotent precursor into lineage-specified pancreatic endodermal tissue encompasses multiple steps. Here, verified iPS cells were treated first with activin A and Wnt3a for generation of definitive endoderm cells, and then with FGF10 and CYC for derivation of gut tube endoderm (FIG. 5A). Derived cells were further treated with FGF10, RA, and CYC in the absence or presence of ILV for generation of pancreatic endoderm, followed by culture in HGF, IGF, and DAPT in the absence or presence of GLP-1 for generation of pancreatic hormone-expressing cells (FIG. 5A). In this way, human iPS clones were induced to form definitive endoderm by treatment with activin A and Wnt3a initially for 1 day followed by culture in activin A and 2% FBS for 2 additional days. Immunostaining of treated cells revealed efficient SOX17 and FOXA2 induction, markers of definitive endoderm (FIG. 5B). Similar results were observed with clones generated from human cardiac fibroblasts or foreskin (FIG. 6). Flow cytometry demonstrated that 92%, 72%, and 84% cells were positive for SOX17 in three distinct clones, respectively (FIGS. 5C and 6). Next, the efficiency of definitive endoderm transformation into pancreatic endoderm was evaluated. Initial attempts to generate pancreatic endoderm cells with FGF10 and CYC for two days, followed by FGF10, RA, and CYC stimulation resulted in cells with low levels of PDX1 expression (data not shown). ILV, which is described elsewhere (Chen et al., Nat. Chem. Biol., 5:258-265 (2009) and Borowiak et al., Cell Stem Cell, 4:348-358 (2009)), was included in the protocol. In the protocol, treatment of iPS-derived definitive endoderm cells with FGF10, RA, and CYC in the presence of ILV resulted in cells expressing PDX1, NEUROD1, and NGN3, markers of pancreatic endoderm (FIG. 5D). Similar results were observed for iPS cells derived from human cardiac fibroblasts or foreskin (FIG. 7). These results demonstrate the successful induction of pancreatic endoderm from iPS-derived definitive endoderm.

Induction of Stage-Specific Pancreatic Genes through Guided Differentiation

To determine the expression of endocrine-specific transcription factors and pancreas-specific genes throughout differentiation, the gene expression pattern was analyzed at each stage of differentiation. RT-PCR detected high levels of FOXA2 expression after 3 days of differentiation, confirming induction of definitive endoderm cells (FIG. 8A). The expression of the endocrine progenitor-specific gene, NGN3, was observed from day 3 of differentiation, and the expression persisted throughout the differentiation process (FIG. 8A). Expression of the islet specific gene, ISL-1, was also found from day 3, with expression levels increasing at later time points (FIG. 8A). Moreover, PDX1 and NEUROD1 transcripts, which were found only after treatment with FGF10, RA, CYC, and ILV, further confirmed the generation of iPS-derived pancreatic endoderm cells upon differentiation (FIG. 8A). To evaluate whether human iPS-derived pancreatic endoderm cells are capable of generating functional pancreatic islet-like cells, an additional step of differentiation was used. The iPS-derived pancreatic endoderm were initially treated with HGF, IGF, Exendin-4, and DAPT; however, resulting cells failed produce detectable C-peptide secretion (data not shown). GLP-1, which is described elsewhere (Buteau et al., Diabetes, 52:124-132 (2003)) was included. Following inclusion of GLP-1, RT-PCR revealed positive gene expression of pancreatic hormones, including insulin, glucagon (GCG), and somatostatin (SST), and islet cell-specific marker genes PDX1, NKX6.1, ISL1, and NEUROD1 and glucose transporter 2 (GLUT2) (FIG. 8A). Conversely, to determine whether pluripotency genes were silenced during differentiation, RT-PCR analysis was performed for c-MYC, GDF3, hTERT, NANOG, SOX2, and KLF4. It was found that c-MYC, GDF3, hTERT, and NANOG gene expression levels gradually decreased during differentiation, while these gene transcripts were absent in the human pancreas (FIG. 8B). SOX2 and KLF4 gene expression remained throughout iPS differentiation, in line with expression of these two genes in the human pancreas (FIG. 8B). The targeted down-regulation of pluripotency genes along with sequential expression of pancreas-specific genes collectively indicated that human iPS cells are capable of undergoing guided differentiation in vitro into islet-like cells, with the observed combined expression of GLUT-2, NKX6.1, and NEUROD1 further suggesting derivation of tissue with properties of functional beta cells.

Differentiation of iPS Cells into Insulin-Secreting Islet-like Progeny

During treatment with RA, FGF10, CYC, and ILV, iPS-derived pancreatic endoderm cells started to form spheroid-like cell clusters, which reached maximum size and number following further maturation with HGF, IGF, DAPT, and GLP-1 (FIG. 8C). The three dimensional morphology resembled pancreatic islet-like clusters (Ramiya et al., Nat. Med., 6:278-282 (2000)), and selected clones yielded clusters (FIG. 8C) strongly positive for C-peptide expression (FIG. 8D). Importantly, even iPS-derived islet-like cells that did not organize into typical clusters also expressed insulin, C-peptide, and glucagon (FIG. 8E). The presence of insulin/C-peptide co-expressing cells (FIG. 9A (i)) confirmed the potential for de novo insulin synthesis and excluded the possible artifact of insulin uptake from the media. Also, insulin-glucagon double positive cells were not observed, indicating that the expression pattern of iPS-derived hormone-expressing islet-like cells is consistent with normal pancreatic beta-cell development. Although few insulin and somatostatin double-positive cells were found (FIG. 9A(ii)), characteristic of immature islet cells, the results provided herein indicate successful differentiation of iPS cells into hormone-expressing islet-like cells. Indeed, similar to pancreatic beta cells, which co-express insulin and PDX1, the majority of the insulin-expressing cells exhibited nuclear-localized PDX1 signals (FIG. 9A (iii)). When the insulin-positive population was quantified by flow cytometry, 1.3%, 0.7%, and 0.8% of distinct clones-derived islet-like cells were insulin-positive (FIGS. 9B and 10).

Functional Response of iPS-derived Islet-like Clusters

C-peptide secretion from iPS-derived islet-like clusters in response to glucose challenge, the critical physiological function of pancreatic beta cells, was analyzed. To determine whether islet-like cells are capable of C-peptide secretion in response to glucose induction, cells were exposed to increasing concentrations of glucose and secreted C-peptide was measured by ELISA. At extracellular glucose levels of 2.5 mM, that mimics a fasting condition, there was only marginal detection of the C-peptide signal (FIG. 9C). Raising glucose levels to 10 mM induced marked secretion of C-peptide by iPS-derived islet-like cells (FIG. 9C). Further raising glucose levels to the supraphysiological 27.7 mM range, triggered an additional bolus of secreted C-peptide, reaching cumulatively the range of 72.0-236.1 pM (HCF #1, three independent experiments, FIG. 9C) or 12.1-50.9 pM (BJ #1). iPS-derived islet-like cells differentiated without ILV or GLP-1 failed to secrete C-peptide in response to glucose challenge (FIG. 9D). Although clonal variation in responsiveness was observed, iPS-derived islet-like clusters were typically capable to secrete C-peptide in response to glucose stimulation.

Example 2

Induced Pluripotent Stem Cells From GMP-Grade Hematopoietic Progenitor Cells and Monocytes Cells Clinical grade peripheral blood hematopoietic progenitor cells (HPC) products from patients, who were deceased, were used. HPCs were harvested from patients following mobilization by injection with granulocyte-CSF for 5 days. Blood (10-20 L) was processed for HPC collection. PBMCs from healthy donors were obtained as described elsewhere (Noser et al., *J. Virol.*, 80:7769-7774 (2006)).

Lentiviral Vector Production

Pluripotency-associated factor-expressing lentiviral vectors, pSIN-OCT4, pSIN-SOX2, pSIN-KLF4, and pSIN-cMYC, were described elsewhere (Nelson et al., *Clin. Transl. Sci.*, 2:118-126 (2009)). These vectors were produced by transient transfection of 293T cells. Vector titers were determined by immunostaining (Nelson et al., *Clin. Transl. Sci.*, 2:118-126 (2009)).

iPSC Derivation

HPCs and PBMCs were cultured overnight in StemSpan H3000 serum-free medium (StemCell Technologies), which contained only human-derived or recombinant human proteins, supplemented with StemSpan CC100 cytokine cocktail (StemCell Technologies). Cultures were then transduced with four sternness factor-expressing lentiviral vectors overnight. One third of the culture supernatants were carefully removed and replaced daily with H3000 growth medium supplemented with CC100 cytokine cocktail. At 3 days after vector infection, cells were transferred to Matrigel (BD Bioscience)-coated culture plates. Starting 5 days after vector infection, cells were maintained in HEScGRO medium (100 mL, Millipore) supplemented with mTeSR-1 maintenance media (25 mL, Stemcell Technologies) (Thatava et al., *Gene Ther.*, 18:283-293 (2011)). Seven to ten days after vector infection, the reprogrammed cells began to form colonies with iPS morphology. At two to three weeks after vector infection, cultures were treated with Cell Dissociation Buffer (Invitrogen) for 5 to 10 minutes to help lift clones, and individual iPSC-like clones were carefully picked up by a P200 pipette and placed into Matrigel-coated wells in a 96-well plate. To prevent spontaneous differentiation, the iPSC culture medium was replaced daily, and differentiated cells in the cultures were manually removed with a pipette tip. As the clones grew, cultures were expanded into larger culture plates for further characterization. Clones were preserved using Xeno-FREEze™ Human Embryonic Stem Cell Freezing Medium (Millipore). A verified iPSC clone, HCF1, from primary human fibroblast (HCF) cells, was described elsewhere (Thatava et al., *Gene Ther.*, 18:283-293 (2011)). Primary human keratinocytes and keratinocyte-derived iPSC clones were also used as controls.

Immunostaining and Alkaline Phosphatase Staining

For immunostaining of iPSC, cells were fixed for 20 minutes at room temperature in 4% paraformaldehyde solution in PBS, washed several times in PBS, and blocked for 30 minutes in PBS with 5% fetal bovine serum. Cells were then stained with primary antibodies overnight at 4° C., rinsed by PBS, and incubated with secondary antibodies for 1 hour at room temperature. For immunostaining of differentiated cells, cells at different stages of differentiation were fixed and stained with primary and secondary antibodies. Primary antibodies used for characterization of iPSC and iPSC-derived cells were: SSEA-4 and TRA-1-60 (Millipore #SCR001), OCT4 (Cell Signaling Technology #2750), NANOG (Abcam #ab21624), mouse anti-SOX17 (R&D Systems #MAB1924), rabbit anti-HNF3 beta/FOXA2 (Millipore #07-633), rabbit anti-PDX1 (Santa Cruz Biotechnology #sc-25403), and mouse anti-insulin (Sigma #12018). Texas Red-conjugated donkey-anti-rabbit IgG (Jackson Laboratories #711-075-152), Texas Red-conjugated donkey-anti-mouse IgG (Jackson Laboratories #715-075-151), FITC-conjugated donkey-anti-rabbit IgG (Jackson Laboratories #711-095-152), and FITC-conjugated donkey-anti-mouse IgG (Jackson Laboratories #715-095-151) were used as secondary antibodies. DAPI was used for counter staining Stained cells were analyzed using confocal laser-scanning microscope (Zeiss, LSM 510 confocal scanning laser system).

Spontaneous Differentiation

For spontaneous differentiation, iPSC clones were dissociated using collagenase IV for 30 minutes and plated on low adhesion plates in basal HEScGRO medium without bFGF. Embryoid bodies (EBs) were cultured as suspension for 7-10 days and adherent in DMEM with 20% FBS for additional 7-10 days. For immunofluorescence analysis, cells were fixed with 4% PFA for 20 minutes at room temperature. Immunostaining was performed as described above. Primary antibodies against FOXA2 for endoderm, beta-III tubulin (Abcam #41489) for ectoderm, and CD31 (Santa Cruz Biotechnology #SC1506) for mesoderm were used, while Texas Red-conjugated donkey anti-rabbit IgG (Jackson Laboratories #711-075-152), and FITC-conjugated donkey anti-chicken IgG (Jackson Laboratories #703-095-155) served as secondary antibodies.

In Vivo Differentiation of Derived iPS Cells

SCID-beige mice were anesthetized, and the kidney was externalized for iPS transplantation under the kidney capsule. A small incision was made in the kidney capsule, and a blunt needle was used to create a pocket under the kidney capsule. Following iPSC injection into the pocket, the kidney was placed back into the abdomen, and the incision closed with vicryl suture. Mice were maintained for 4 weeks and sacrificed for harvesting normal and iPS-transplanted kidneys. OTC-embedded frozen tissues were cryo-sectioned for H&E staining Differentiation of Derived iPS Cells Into Insulin Producing Cells iPSC were differentiated into insulin-producing cells as reported elsewhere with several modifications (Thatava et al., *Gene Ther.*, 18:283-293 (2011)). At the first step of differentiation, human iPSC clones were treated with 25 ng/mL Wnt3a (R&D systems) and 100 ng/mL activin A (Peprotech) in advanced RPMI (Invitrogen) with Pen/Strep for 1 day, followed by treatment with 100 ng/mL activin A in advanced RPMI supplemented with 0.2% fetal calf serum (FCS) (Invitrogen) for two days. At step two, cells were cultured in high glucose DMEM (Invitrogen), supplemented with 20% (v/v) advanced RPMI medium containing 50 ng/mL FGF10 (R&D systems), 0.25 µM KAAD-cyclopamine (CYC), and 2% FCS for 2 days. Cells were then treated with 50 ng/mL FGF10, 0.25 µM CYC, and 2 µM all-trans Retinoic Acid (RA) (Sigma) in high glucose DMEM (Invitrogen) supplemented with 20% advanced RPMI, Pen/Strep, 1× B27 supplement (Invitrogen) for 4 days at step three. Cells were then cultured in the presence of 50 ng/mL FGF10, 300 nM ILV (Axxora), and 55 nM GLP-1 (Sigma) in DMEM (high glucose) supplemented with 20% advanced RPMI and 1× B27 for 4 days at step four. In step five, differentiation medium included 10 µM DAPT (Sigma) and 55 nM GLP-1 in DMEM (high glucose) with 20% advanced RPMI and 1× B27 and culture lasted 6 days. Finally, in step six, cells were cultured in the presence of 50 ng/mL hepatocyte growth factor (HGF) (R&D systems), 50 ng/ml insulin-like growth factor 1 (IGF-1) (R&D systems), and 55 nM GLP-1 in CMRL-1066 medium (Invitrogen) with 1× B27 for 8 days. All differentiation experiments were performed in triplicate, and repeated at least two times.

Microarray

Total RNA was isolated using TRIzol (Invitrogen) and further purified using RNeasy Plus spin columns (QIAGEN). Turbo DNA-free DNase (Ambion, Austin, Tex.) was used to digest all genomic DNA that could lead to false positive gene expression results. The RNA quantity and purity was measured with a Nanodrop spectrophotometer (Thermo Scientific, Wilmington, Del.), and the RNA integrity was determined using the Agilent 2100 Bioanalyzer (Santa Clara, Calif.). Microarray analysis was performed using the Affymetrix HG-U133 Plus2 GeneChip Array platform (Affymetrix, Santa Clara, Calif.). Data were preprocessed using standard in-house MicroArray Pre-Processing workflow, and hierarchical clustering was performed by Pearson Dissimilarity. To compare the transcriptome of blood-derived iPSCs, the data set of epidermal keratinocytes (HK, SW3, SW4 and SW8), two keratinocyte-derived iPSC clones (SW3 #b and SW4 #N1), and human fibroblast (FB)-derived iPSC clone HCF1 (Thatava et al., *Gene Ther.*, 18:283-293 (2011)) were used. T-test was performed to analyze the significance of the changes (p<0.05) in the normalized gene expression levels between HK and iPSC clones, or between blood-derived iPSC clones and HK- and FB-derived iPSC clones.

Heatmap Builder software (provided by Dr. Euan Ashley, Stanford School of Medicine) was used to generate a heatmap for the transcriptome data set. The registered GEO transcriptome database (GSM551202, human ES H9 cells; GSM452255, freshly isolated PBMC; GSM178554, mobilized HPCs) were used to analyze the similarities between blood-derived iPSC and human ES cells or non-reprogrammed PBMCs and HPCs.

Results

Cellular reprogramming of HPCs and PBMCs into iPSCs

HPCs and PBMCs were cultured overnight in a serum-free medium with CC100 cytokine cocktail (recombinant Flt-3, SCF, IL-3 and IL-6), and transduced with four stemness factor-expressing lentiviral vectors at an MOI of 5 each. When transduced cells were transferred to Matrigel-coated culture plates at day 3 post-infection, a subset of cells attached to the plate. At 1 to 2 weeks after vector transduction, small, reprogrammed colonies, characterized by the morphology of sharp-edged, flat and tightly-packed cells, were observed (FIG. 11A). No iPSC-like colony formation was observed in untransduced cells (FIG. 11A). Individual iPSC-like colonies were picked based on their size and morphology at 2 to 3 weeks after viral transduction and expanded under feeder-free conditions. The number of iPS-like colonies, expanded without substantial spontaneous differentiation, was between 2 to 10 clones per $10^5$ transduced cells (FIG. 11B). HPC- and PBMC-derived iPS clones were capable of being cultured for 5 months after the initial vector infection (up to passage 50) without showing signs of replicative crisis. Immunocytochemistry revealed the expression of SSEA-4, TRA-1-60, OCT4, and NANOG in the blood-derived iPSC clones (FIG. 11B). Long-term time-lapse imaging demonstrated efficient iPSC expansion under feeder-free and serum-free conditions, with a 23.7 hour average cell doubling time (FIG. 12A). Frequent mitotic events were observed in derived iPSC colonies (FIG. 12B), and the duration of mitotic events (from prophase to telophase) was approximately 60 minutes (FIGS. 12B and 12C).

Ultrastructural Studies of Blood-derived iPS Cells

High-resolution electron microscope analysis was performed to determine the morphological differences between blood-derived iPSCs and verified fibroblast-derived iPSCs (HCF1) (Thatava et al., *Gene Ther.*, 18:283-293 (2011)). Blood-derived iPSCs exhibited scant cytoplasm and globular-shaped immature mitochondria with unorganized cristae, which resembled those of fibroblast-derived iPS cells (FIG. 13A). In contrast, non-reprogrammed fibroblasts exhibited the cytoplasm densely packed with membrane-bound organelles (FIG. 13A, upper left panel) including mature mitochondria with well-developed cristae (FIG. 13A, upper right panel). In accordance with the cinemicrography analysis, frequent mitotic events were observed in blood-derived iPSCs cells (FIG. 13B). One pair of centrioles—mother (arrowhead) and daughter (arrow) centrioles—were seen in a dividing cell at anaphase (FIG. 13B, lower right panel).

Genome-wide Transcriptome Analysis of Blood-derived iPS Clones

Using a microarray representing the genome-wide transcriptome, the global gene-expression patterns in HPC- and PBMC-derived iPSC clones were determined, which were then compared with those of fibroblast (FB)- and epidermal keratinocytes (HK)-derived iPSCs. Transcriptome data from non-reprogrammed HK cells were also used as somatic cell controls. The dendrogram of unsupervised one-way hierarchical clustering analysis demonstrated that blood-derived iPSCs clustered closely with other iPSCs from different cell sources and were distinct from non-reprogrammed HK cells (FIG. 14A). In accordance with this observation, the global gene-expression patterns of blood-derived iPSCs were more similar to those in human ES H9 cells and HK-derived iPSCs, rather than non-reprogrammed HSCs or PBMCs (FIG. 14B). Similar to HK- and FB-derived iPSC clones, expression of pluripotency-associated genes, such as OCT4, SOX2, NANOG, LIN28, and TERT, were markedly up-regulated in HPC- and PBMC-derived iPSC clones (FIG. 14C). When the top 100 differentially expressed genes between blood-derived iPSC clones and non-reprogrammed HK cells were analyzed and used to generate heatmaps including FB- and HK-derived iPS cells, the gene expression patterns of blood-derived iPSCs were nearly identical to those of iPSCs derived from FB and HK cells. Among the 200 differentially expressed genes (100 highest and 100 lowest), notable differences in gene expression profiles were only found in XIST (with three probes, FIG. 14D, upper panel), USP9Y, EIF1AY, DDX3Y, and RPS4Y1 (FIG. 14D, lower panel) in two HK-derived iPSC clones (SW3 #b and SW3 #NI). XIST is on the X chromosome and XIST RNA plays a major role in silencing one of the pair of X chromosomes in female cells (Nagano and Fraser, Cell, 145:178-181 (2011)), while USP9Y, EIF1AY, DDX3Y, and RPS4Y1 are Y-linked genes. Since HK and HK-derived iPSC clones were from female patients, while HCF1, HPC-A1, PBMC-S1 and PBMC-S2 were from male patients, the observed variations in X- and Y-linked genes between blood- and non-blood-derived iPSC clones were likely due to the difference in gender of these iPSC clones.

Pluripotency of Blood-derived iPS Clones Verified Through In Vitro Differentiation HPC- and PBMC-derived iPSC clones were assayed for the ability to spontaneously differentiate in vitro into cells of three embryonic germ layers through embryoid body (EB) formation. All the iPSC clones assayed formed EBs. After 7 to 10 days in suspension, EBs were transferred to a Matrigel-coated plate, and spontaneously differentiated cells were expanded under adherent conditions. Immunostaining for lineage-specific markers revealed that blood-derived iPSCs differentiated into cells of three germ layers including beta-III tubulin-positive ectoderm, FOXA2-positive endoderm, and CD31-positive mesoderm cells (FIG. 15A).

In Vivo Multilineage Differentiation of Blood-derived iPSCs

To assess the multilineage differentiation capacity of iPSCs in vivo, blood-derived iPSCs were transplanted under the kidney capsule of SCID-beige mice. Following transplantation of 1 million cells, iPSCs formed cystic tumors within 4 weeks (FIG. 13B). Upon gross inspection, iPSC-derived tumors demonstrated a complex cellular architecture with prominent vascularization and nonvascularized solid tissues. Histological analysis revealed iPSC differentiation into endoderm lineages composed of glandular-like tissue, mesoderm lineages indicated by muscle-like tissue and ectoderm lineages denoted by neural rosette-like structures (FIG. 15B), which verified the multi-lineage differentiation capability of blood-derived iPSCs.

Generation of Insulin-producing Cells From iPSCs Through Guided Differentiation

The pancreatic differentiation potentials of blood-derived iPSCs was examined. A guided iPSC differentiation protocol with indolactam V (ILV) and GLP-1 was used as set forth above. Blood-derived iPSC clones were first stimulated with actin A and Wnt3a to form definitive endoderm cells. Immunostaining revealed the efficient induction of definitive endoderm markers SOX17 and FOXA2 in iPSC-derived cells at day 5 of differentiation (FIG. 13C). Derived definitive endoderm cells were further differentiated in DMEM/advanced RPMI medium containing FGF10, CYC, and 2% FBS (v/v) for 2 days, and maintained in high glucose DMEM/advanced RPMI medium supplemented with FGF10, CYC, RA, and 1 x B27 for an additional 4 days. Cells were then cultured in the presence of FGF10, ILV, GLP-1, and 1 x B27 in DMEM/advanced RPMI medium for 4 days. After this step, derived cells expressed pancreatic endoderm markers, PDX1 and NKX6.1 (FIG. 15D). Further differentiation of iPSC-derived pancreatic endoderm cells was performed in DMEM/advanced RPMI medium supplemented with DAPT, GLP-1, and 1× B27 for 6 days, followed by the final maturation step in the CMRL-1066 medium containing HGF, IGF-1, GLP-1, and 1× B27 for an additional 8 days. Insulin-positive iPSC progeny were sporadically detected (FIG. 15D). High levels of intracellular C-peptide (230-320 pM), a byproduct of proinsulin processing during insulin secretion, were also detected in the final differentiation stage iPSC progeny by C-Peptide ELISA. These results demonstrate successful differentiation of blood-derived iPSCs into insulin-expressing cells in vitro.

The results provided herein demonstrate the feasibility of iPSC derivation from GMP-grade mobilized HPCs and unmobilized PBMCs. The use of HPCs and PBMCs enabled time-effective iPSC derivation, as the cells did not require long-term expansion before reprogramming. Moreover, apart from minor differences in global gene expression profiles (FIG. 14), blood-derived iPSCs were basically indistinguishable from iPSCs from other cell sources. Considering that many institutes/hospitals already have FDA-approved GMP facility for autologous HPC processing, HPCs and PBMCs can be used as described herein as ideal somatic cell sources for clinical-grade iPSC derivation.

The results provided herein also demonstrate the feasibility of generating insulin-producing cells from blood-derived iPSCs. In contrast to skin biopsies, which involve an invasive procedure, the use of blood cells allows minimally invasive tissue procurement for iPSC derivation. Since diabetic patients often experience poor wound healing, the minimally invasive iPSC derivation from blood cell sources would be particularly advantageous for the generation of clinical-grade iPSCs from diabetic patients.

Example 3

Reprogrammed Keratinocytes From Elderly Type 2 Diabetes Patients Suppress Senescence Genes to Acquire Induced Pluripotency Human Keratinocytes Skin specimens from surgical pathology from nondiabetic and type 2 diabetic (T2D) individuals were enzymatically processed. Using sterile techniques, skin samples were incubated overnight at 4° C. in dispase (25 U/mL) to cleave epidermis from dermis. The epidermal layer was then placed into a recombinant trypsin/EDTA solution (Invitrogen, Carlsbad, CA,) and incubated for 30 min at 37° C. Trypsin/EDTA was neutralized with a trypsin inhibitor (Invitrogen, Carlsbad, CA), and epidermal pieces were pipetted to release epidermal cells. The suspension was then passed through a 70 µm cell strainer and pelleted. Cell viability was determined by the trypan blue exclusion method. Cells were seeded in a plate coated with an animal component-free (ACF) coating matrix (Invitrogen). Selective trypsinization removed fibroblasts at about 6 minutes, while human keratinocytes (HK) were dissociated at about 20 minutes. HK cell populations were then grown in EpiLife Medium and S7 growth supplement (Invitrogen, Carlsbad, Calif.) in 5% $CO_2$ and 95% air at 37° C. HK cells were maintained semi-confluent in low calcium media.

Reprogramming

Lentiviral vectors, pSIN-OCT4, pSIN-SOX2, pSIN-KLF4, and pSIN-cMYC, were manufactured as described elsewhere to express pluripotency factors from an internal spleen focus-forming virus (SFFV) promoter (Nelson et al., Clin. Trans'. Sci., 2:118-126 (2009)). HIV vectors were produced by transient transfection of 293T cells. To minimize calcium-mediated differentiation of HK cells during vector infection, lentiviral vectors were concentrated by ultracentrifugation and re-suspended in PBS (Sakuma et al., Hum. Gene Ther., 21:1665-1673 (2010)). Lentiviral titers were determined by immunostaining (Nelson et al., *Clin. Transl. Sci.*, 2:118-126 (2009)). Human HK cells were grown in vitro in ACF EpiLife Medium in a matrix-coated plate. Cultures were transduced overnight with human OCT4, SOX2, KLF4, and cMYC expressing lentiviral vectors (Nelson et al., *Clin. Transl. Sci.*, 2:118-126 (2009)). Culture supernatants were replaced daily with ACF media. At 4 days after vector infection, media was changed to HEScGRO medium (100 mL, Millipore, Billerica, Mass.) supplemented with mTeSR-1 maintenance media (25 mL, Stemcell Technologies, Vancouver, BC, Canada) (Thatava et al., *Gene Ther.*, 18:283-293 (2011)). One to two weeks after vector infection, reprogrammed cells began to form colonies displaying stem cell morphology (Thatava et al., *Gene Ther.*, 18:283-293 (2011)). At three to four weeks after vector infection, cultures were treated with Cell Dissociation Buffer (Invitrogen, Carlsbad, Calif.) for 5 to 10 minutes to help lift clones picked by a P200 pipette, and placed in BD Matrigel (BD Biosciences, San Jose, Calif.) coated 96-well plates. To prevent spontaneous differentiation, the iPS culture medium was replaced daily and differentiated cells in cultures manually removed. As clones grew, cultures were expanded into larger culture plates for further characterization. iPS clones were preserved using Xeno-FREEze™ Human Embryonic Stem Cell Freezing Medium (Millipore, Billerica, Mass.). For spontaneous differentiation, iPS clones were dissociated using collagenase IV (Stemcell Technologies) for 30 minutes and plated on low adhesion plates in basal HEScGRO medium without bFGF. Embryoid bodies (EBs) were cultured as suspensions for 7-14 days, and grown adherent in DMEM with 20% FBS for additional 7-14 days.

Differentiation of iPS Cells Into Insulin-producing Cells iPS clones were treated with 25 ng/mL Wnt3a (R&D systems) and 100 ng/mL activin A (Peprotech) in advanced RPMI (Invitrogen) with Pen/Strep for 1 day, followed by treatment with 100 ng/mL activin A in advanced RPMI supplemented with 0.2% fetal calf serum (FCS) (Invitrogen) for two days. Next, cells were cultured in high glucose DMEM (Invitrogen), supplemented with 20% (v/v) advanced RPMI medium containing 50 ng/mL FGF10 (R&D systems), 0.25 µM KAAD-cyclopamine (CYC), and 2% FCS for 2 days. Cells were then treated with 50 ng/mL FGF10, 0.25 µM CYC, and 2 µM all-trans Retinoic Acid (RA) (Sigma) in high glucose DMEM (Invitrogen) supplemented with 20% advanced RPMI, Pen/Strep, 1× B27 supplement (Invitrogen) for 4 days. Cells were then cultured in 50 ng/mL FGF10, 300 nM ILV (Axxora), and 55 nM GLP-1 (Sigma) in DMEM (high glucose) supplemented with 20% advanced RPMI and 1× B27 for 4 days. Differentiation medium including 10 µM DAPT (Sigma) and 55 nM GLP-1 in DMEM (high glucose) with 20% advanced-RPMI and 1× B27 was used to culture cells for the next 6 days. Finally, cells were cultured in 50 ng/mL hepatocyte growth factor (HGF) (R&D systems), 50 ng/mL insulin-like growth factor 1 (IGF-1) (R&D systems), and 55 nM GLP-1 in CMRL-1066 medium (Invitrogen) with 1 × B27 for 8 days.

Immunostaining

For immunostaining, iPS cells were fixed for 20 minutes at room temperature in 4% paraformaldehyde (PFA), washed in PBS, and blocked for 30 minutes in PBST (PBS with 0.1% Tween-20 (Sigma) and 5% FBS). Cells were stained with primary antibodies overnight at 4° C., rinsed by PBS, and incubated with secondary antibodies for 1 hour at room temperature. Separately, cells at different stages of differentiation were fixed and stained with primary and secondary antibodies. Primary and secondary antibodies used for characterization were: SSEA-1, SSEA-4, TRA-1-60, TRA-1-81 (Millipore #SCR001), OCT4 (Cell Signaling Technology #2750), SOX2 (Cell Signaling Technology #2748), KLF4 (Abcam #ab26648), NANOG (Abcam #ab21624), anti-SOX17 (R&D Systems #MAB1924), anti-HNF3 beta/FOXA2 (Millipore #07-633), anti-PDX1 (Santa Cruz Biotechnology#sc-25403), and anti-insulin (Sigma #12018). Texas Red-conjugated anti-rabbit IgG (Jackson Laboratories #711-075-152), Texas Red-conjugated anti-mouse IgG (Jackson Laboratories #715-075-151), FITC-conjugated anti-rabbit IgG (Jackson Laboratories #711-095-152), and FITC-conjugated anti-mouse IgG (Jackson Laboratories #715-095-151) were used as secondary antibodies. DAPI was used to counter-stain nuclei. Stained cells were analyzed using confocal laser-scanning microscopy (Zeiss, LSM 510 confocal scanning laser system). Alkaline phosphatase staining was performed with an Alkaline Phosphatase Detection Kit (Millipore). Antibodies FOXA2 for endoderm, beta III tubulin (Abcam #41489) for ectoderm and CD31 (Santa Cruz Biotechnology #SC1506) for mesoderm were used to immunostain embryoid body-derived cells.

In Vivo Differentiation of iPS Cells

SCID-beige mice were anesthetized, and the kidney exposed for iPS transplantation under the kidney capsule. To this end, a small incision was made in the kidney capsule, and a blunt needle was used to create a pocket under the kidney capsule. Following iPS cell injection, the kidney was placed back into the abdomen, and the incision closed. Mice were maintained for 4 weeks and sacrificed for harvesting normal and iPS-transplanted kidneys. OTC-embedded frozen tissues were cryo-sectioned for H&E staining Gene expression For amplification of mitochondrial DNA, mitochondria-specific primer pairs (CYTB, CCTAGCCATGCACTACT-CACCAGACGCCT (SEQ ID NO:39), CTGTCTACT-GAGT-AGCCTCCTCAGATTC (SEQ ID NO:40); and NADH, TCACCAAAGAGCCCCTAA-AACCCGCCA-CATCTA (SEQ ID NO:41), TAAGGGTGGAGAGGT-TAAAGGAGC (SEQ ID NO:42)) were used. For RT-PCR analysis, total RNA was isolated using TRIzol (Invitrogen), and reverse transcription was performed with oligo (dT) primer using RNA to cDNA EcoDry (Clontech). Platinum Taq DNA polymerase (Invitrogen) and primer pairs for TERT (TGTGCACCAACATCTACAAG (SEQ ID NO:43), GCGTTCTTGGCTTTCAGGAT (SEQ ID NO:44)), INS (AGCCTTTGTGAACCAACACC (SEQ ID NO:45), GCTGGTAG-AGGGAGCAGATG (SEQ ID NO:46)), SST (GTACTTCTTGGCAGAGCTGCTG (SEQ ID NO:47), CAGAAGAAATTCTTGCAGCCAG (SEQ ID NO:48)), GCG (AGGCAGACC-CACTCAGTGA (SEQ ID NO:49), AACAATGGCGACCTCTTCTG (SEQ ID NO:50)), GLUT2 (GCTACCGACAGCCTATTCTA (SEQ ID NO:51), CAAGTCCCACTGACATGAAG (SEQ ID NO:52)), and α-tubulin (AAGAAGTCCAAGCTGGAGTTC (SEQ ID NO:53), GTTG-GTCTGGAATTCTGTCAG (SEQ ID NO:54)) were used for the reaction. Separately, total RNA was isolated using TRIzol (Invitrogen) and further purified using RNeasy Plus spin columns (QIAGEN). Turbo DNA-free DNase (Ambion, Austin, TX) was used to digest all genomic DNA that could lead to false positive gene expression results. RNA quantity and purity were measured with a Nanodrop spectrophotometer (Thermo Scientific, Wilmington, Del.), and RNA integrity was determined using the Agilent 2100 Bioanalyzer (Santa Clara, Calif.).

Microarray analysis was performed using the Affymetrix HG-U133 Plus2 GeneChip Array platform (Affymetrix, Santa Clara, CA). Data were preprocessed using MicroArray Pre-Processing workflow, and hierarchical clustering was performed by Pearson Dissimilarity. For comparison of transcriptome data between pre- and post-reprogramming, the data set of parental HK cells from three patients (SW3, SW4 and SW8) were compared with those of three iPS clones from the same patients (SW3 #B, SW4 #N1, and SW8 #20I). Student's t-test was performed to assess significance (p<0.05) in normalized gene expression levels between HK and HK-derived iPS clones. The Heatmap Builder software (provided by Dr. Euan Ashley, Stanford University) was used to generate the heatmap for the transcriptome data set. Enrichment analysis was also performed to match gene IDs in functional ontologies. The registered GEO transcriptome information (GSM551202, human ES H9 cell transcriptome) was used as reference.

Telomere Assay

Total genomic DNA was isolated from patient-derived HK and iPS cells using QIAGEN DNeasy Blood & Tissue Kit. Telomere length was determined using TeloTAGGG telomere length assay (Roche). Genomic DNA digestion, Southern blotting, and chemiluminescence detection was performed as per established protocols. Densitometric analysis was performed on Adobe Photoshop, and terminal restriction fragment lengths were determined by $\Sigma(OD_i/\Sigma(OD_i/L)$, where OD, and L were the optical density and length of fragment, respectively.

Results

Reprogramming of Human Keratinocytes

Lentiviral vectors encoding human OCT4, SOX2, KLF4, and c-MYC, at an approximate multiplicity of infection of 5 each, transduced early passage human keratinocytes (HK cells) derived from 56 to 78 year-old individuals with or without T2D. Under serum-free and feeder-free conditions, within 1 to 2 weeks after viral vector infection, small reprogrammed colonies, characterized by a sharp-edged, flat, tightly-packed morphology, were apparent (FIG. 16A). Individual colonies were picked based on size and morphology at 3 to 5 weeks after viral transduction, and expanded. Structurally derived clones resembled human ES or fibroblast-derived iPS cells and expressed high levels of the stemness marker alkaline phosphatase (FIG. 16B). Immunocytochemistry further validated robust expression of diverse pluripotency markers, including SSEA-4, TRA-1-60, TRA-1-81, OCT4, SOX2, KLF4, and NANOG in HK-derived iPS clones regardless of patient age and status of diabetes (FIG. 16C). The obtained yield was 2 to 10 expandable clones per $10^5$ transduced cells with maintained pluripotent markers and absence of replicative crisis even at 7 months post-initial vector infection (up to passage 60).

Differentiation Propensity of Derived iPS Cells

HK-derived iPS clones from diabetic and non-diabetic patients spontaneously differentiated in vitro into cells of all three germ layers within embryoid body (EB) formations (FIG. 17). In line with acquired pluripotency, HK-derived iPS cells differentiated into ectoderm (beta-III tubulin), endoderm (FOXA2), and mesoderm (CD31) as detected by immunostaining for lineage-specific markers (FIG. 17A). Clonal, rather than inter-patient, variations in differentiation propensities was observed within the tested cohort (FIG. 17A). Moreover, in vivo HK-derived iPS cells transplanted under the kidney capsule of SCID-beige mice at a dose of 1 million cells gave rise to 1-2 cm outgrowth within 4 weeks (FIG. 17B). Tissue histology revealed iPS differentiation into mesoderm lineages indicated by muscle and adipocytes (FIG. 17C), ectoderm lineages denoted by neuroepithelium-like tissues (FIG. 17C), and endoderm lineages composed of glandular tissue (FIG. 17C). These data document multilineage propensity of HK-derived iPS cells from both diabetic and non-diabetic patients across tested age groups.

Genome-wide Transcriptome Switch Underlies Transition to Induced Pluripotency

Unbiased scan of the genome-wide transcriptome revealed distinct global gene-expression patterns in parental HK versus HK-derived iPS clones (FIG. 18). The dendrogram of unsupervised one-way hierarchical clustering analysis demonstrated that HK-derived iPS cells from different patients clustered together, and branched out from parental origin (FIG. 18A). Consistent with acquisition of a pluripotent transcriptome, gene expression patterns of HK-derived iPS cells were overall similar to those of human ES H9 cells, and different from parental counterparts (FIG. 18B). Induction of key pluripotency genes, such as OCT4, SOX2, NANOG, LIN28, telomerase (TERT), DPPA4, and PODXL, were also evident in iPS clones (FIG. 18C). Further analysis revealed upon reprogramming significantly up-regulated proto-oncogenes (N-MYC and KIT), pluripotency-maintenance factor FGF-2, and the receptor for FGF-2 (FGFR1), whereas cytoskeletal and keratin-encoding genes were down-regulated across HK-derived iPS clones (FIG. 18D). Similar to ES cells, which are known to express minimal levels of MHC class I genes, HK-derived iPS cells exhibited marked down-regulation of these genes (FIG. 18E). Bioinformatic analysis of transcriptome data identified pathways involved in epithelial-to-mesenchymal transition and cytoskeletal remodeling as most significantly affected networks in response to reprogramming of HK cells, in line with genuine redirection of cell fate. No notable difference was observed in the transcriptome of iPS clones from non-diabetic and diabetic patients.

Ultrastructural Remodeling Induced by Reprogramming

Electron microscopy demonstrated marked difference in the size of derived iPS compared to parental HK (FIG. 19). Parental HK cells were 25 to 40 μm in diameter, while derived iPS cells were 10 to 15 μm, characterized by scant cytoplasm and regularly condensed chromatin (FIG. 19A) with frequent mitotic events (FIG. 19B). The cytosol of HK cells was densely packed with membrane-bound organelles (FIG. 19C, left panel) and keratin intermediate filaments. In sharp contrast, widely distributed, relatively poorly developed endoplasmic reticulum and Golgi stacks were found in iPS clones (FIG. 19C, right panel). In HK cells, mitochondria appeared mainly tubular-shaped and showed well-developed cristae. In contrast, mostly globular immature mitochondrial remnants, characterized by unorganized cristae, were found in HK-derived iPS cells (FIG. 19D) as in verified fibroblast-derived iPS clones (FIG. 19A). No notable difference was observed in morphologies of mitochondria between iPS clones from non-diabetic and diabetic patients.

Reprogramming Down-regulates Mitochondria/Oxidative Stress Signaling Pathway

The copy number of mitochondrial DNA before and after reprogramming revealed a 30 to 60% reduction in the abundance of mitochondrial DNA in iPS compared to HK cells (FIG. 20A). Immunostaining with mitochondrial probes detected mitochondria-specific signals in individual iPS cells (FIG. 20B and 20C) and no significant changes in expression of nuclear-encoded mitochondrial biogenesis factors (FIG. 20D). Selected genes involved in the TCA cycle, such as ACO2, SDHA, and FH, were down-regulated by nuclear reprogramming (FIG. 20E). Transcriptome analysis further revealed that genes encoding the mitochondrial/oxidative stress response pathway are highly expressed in HK cells from elderly patients, yet markedly down-regulated in derived iPS cells (FIG. 20F). Reduced transcription following reprogramming was particularly evident in major antioxidant enzymes (Finkel et al., Nature, 408: 239-247 (2000)), such as catalase CAT and GPX1 (FIG. 20F), suggesting reversal of cellular markers of senescence.

Reprogramming Induces Telomere Elongation and Down-regulates Genes Involved in Senescence RT-PCR verified increased levels of TERT-specific transcripts in HK-derived iPS cells (FIG. 21A). In fact, the telomere restriction fragment (TRF) assay further demonstrated that HK-derived iPS cell lines display longer telomeres than parental HK cells (FIG. 21B), indicating reprogramming induced telomere elongation regardless of diabetes status. Comparison of the transcriptome between three parental HK cells (SW3-HK, SW4-HK, and SW8-HK) and derived iPS clones (SW3 #B, SW4 #N1, and SW8 #20I) revealed significant down regulation (p<0.05) of senescence/apoptosis-associated genes (FIG. 21C), including $p16^{INK4a}$ and $p15^{INK4b}$ in the $p16^{INK4a}$/RB pathway, and $p21^{CIP1}$ in the $p19^{ARF}$/p53 pathway, and proapoptotic genes, including FAS, CASP8, CASP7, BAD, and TP53AIP1 (FIG. 21D). These results indicated that successful cellular reprogramming of somatic cells from elderly patients is associated with suppression of key senescence- and apoptosis-related pathways in diabetic and non-diabetic patients.

Proficiency of HK-derived iPS Cells to Yield Insulin Producing Islet-like Progeny HK-derived iPS clones were initially induced to form definitive endoderm by treatment with activin A and Wnt3a for 1 day followed by culture in activin A and 2% FBS for 4 additional days. Immunostaining revealed efficient induction in iPS-derived cells of SOX17 and FOXA2, markers of definitive endoderm (FIG. 22A). Similar results were observed with iPS clones generated from diabetic or non-diabetic patients. Next, the efficiency of definitive endoderm transformation into pancreatic endoderm was evaluated. As shown in FIG. 22B, prominent nucleus-localized signals for pancreatic endoderm, namely PDX1 and NKX6.1, were found in iPS-derived cells at day 14 of differentiation. No notable difference was found among iPS clones from non-diabetic and diabetic patients. These results indicate successful induction of pancreatic endoderm from HK-iPS-derived definitive endoderm. In the presence of DAPT and GLP-1, iPS-derived pancreatic endoderm cells were further differentiated for 6 days, followed by maturation in HGF, IGF-1, and GLP-1 for additional 8 days. By day 24, insulin-producing cells were sporadically detected in iPS-derived progeny (FIG. 22C), while more prominent immunostaining for insulin was evident after final maturation at day 29 (FIG. 22D and 22E). Similar to pancreatic beta cells which co-express insulin and PDX1, the majority of iPS-derived insulin-expressing cells exhibited nuclear-localized PDX1 signals (FIG. 22D and 22E). High levels of intracellular C-peptide (250-290 pM), a byproduct of proinsulin protein processing, were detected in iPS progeny by ELISA, while RT-PCR revealed positive gene expression of key pancreatic factors, including insulin (INS), glucagon (GCG), and somatostatin (SST), and glucose transporter 2 (GLUT2) (FIG. 22F). Thus, HK-derived iPS cells differentiated into hormone-producing pancreatic islet-like cells.

These results demonstrate the feasibility and reproducibility of iPS cell derivation from elderly patients with T2D. Reprogramming of HK cells was accompanied by morphological changes, induction of endogenous pluripotency genes, telomere elongation, and down-regulation of senescence- and apoptosis-related genes. Notably, stepwise differentiation with ILV and GLP-1 achieved successfully differentiation of T2D-specific iPS cells into insulin-producing islet-like cells. Thus, reprogramming of keratinocytes from elderly T2D patients yields proficient iPS cells through induction of a senescence privileged status. T2D-specific iPS cells can provide a versatile platform for disease modeling and regenerative applications.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for obtaining a population of glucose-responsive, insulin-secreting cells from a diabetic human, wherein said method comprises:
   (a) obtaining somatic cells from a diabetic human,
   (b) exposing said somatic cells to one or more polypeptides or nucleic acids encoding said one or more polypeptides to form induced pluripotent stem cells, wherein said one or more polypeptides are selected from the group consisting of a Oct3/4 polypeptide, a Sox family polypeptide, a Klf family polypeptide, a Myc family polypeptide, a Nanog polypeptide, and a Lin28 polypeptide, and
   (c) culturing said induced pluripotent stem cells with medium comprising indolactam V and glucagon like peptide-1 to obtain said population of glucose-responsive, insulin-secreting cells.

2. The method of claim 1, wherein said medium lacks serum.

3. The method of claim 1, wherein said culturing is performed in the absence of feeder cells.

4. The method of claim 1, wherein said culturing is performed in the absence of non-human feeder cells.

5. The method of claim 1, wherein said somatic cells are selected from the group consisting of skin, lung, heart, stomach, brain, liver, blood, kidney, and muscle cells.

6. The method of claim 1, wherein said induced pluripotent stem cells comprise exogenous nucleic acid encoding a human Oct4 polypeptide, a human Sox2 polypeptide, a human Klf4 polypeptide, and a human c-Myc polypeptide.

7. The method of claim 1, wherein said medium comprises greater than 300 nM of indolactam V.

8. The method of claim 1, wherein said medium comprises greater than 55 nM of glucagon like peptide-1.

9. The method of claim 1, wherein said culturing is performed for four days.

* * * * *

SEQUENCE LISTING

<160> NUMBER OF SEQ ID NOS: 54

<210> SEQ ID NO 1
<211> LENGTH: 20
<212> TYPE: DNA
<213> ORGANISM: Homo sapiens

<400> SEQUENCE: 1
agcgaaccag tatcgagaac                                          20

<210> SEQ ID NO 2
<211> LENGTH: 20
<212> TYPE: DNA
<213> ORGANISM: Homo sapiens

<400> SEQUENCE: 2
ttacagaacc acactcggac                                          20

<210> SEQ ID NO 3

```
<211> LENGTH: 20
<212> TYPE: DNA
<213> ORGANISM: Homo sapiens

<400> SEQUENCE: 3
agctacagca tgatgcagga                                               20

<210> SEQ ID NO 4
<211> LENGTH: 20
<212> TYPE: DNA
<213> ORGANISM: Homo sapiens

<400> SEQUENCE: 4
ggtcatggag ttgtactgca                                               20

<210> SEQ ID NO 5
<211> LENGTH: 20
<212> TYPE: DNA
<213> ORGANISM: Homo sapiens

<400> SEQUENCE: 5
tgaacctcag ctacaaacag                                               20

<210> SEQ ID NO 6
<211> LENGTH: 20
<212> TYPE: DNA
<213> ORGANISM: Homo sapiens

<400> SEQUENCE: 6
tggtggtagg aagagtaaag                                               20

<210> SEQ ID NO 7
<211> LENGTH: 20
<212> TYPE: DNA
<213> ORGANISM: Homo sapiens

<400> SEQUENCE: 7
actctgagga ggaacaagaa                                               20

<210> SEQ ID NO 8
<211> LENGTH: 19
<212> TYPE: DNA
<213> ORGANISM: Homo sapiens

<400> SEQUENCE: 8
tggagacgtg gcacctctt                                                19

<210> SEQ ID NO 9
<211> LENGTH: 20
<212> TYPE: DNA
<213> ORGANISM: Homo sapiens

<400> SEQUENCE: 9
tctcaaggca cacctgcgaa                                               20

<210> SEQ ID NO 10
<211> LENGTH: 20
<212> TYPE: DNA
<213> ORGANISM: Homo sapiens

<400> SEQUENCE: 10
tagtgcctgg tcagttcatc                                               20
```

```
<210> SEQ ID NO 11
<211> LENGTH: 20
<212> TYPE: DNA
<213> ORGANISM: Homo sapiens

<400> SEQUENCE: 11
tgtgcaccaa catctacaag                                               20

<210> SEQ ID NO 12
<211> LENGTH: 20
<212> TYPE: DNA
<213> ORGANISM: Homo sapiens

<400> SEQUENCE: 12
gcgttcttgg ctttcaggat                                               20

<210> SEQ ID NO 13
<211> LENGTH: 20
<212> TYPE: DNA
<213> ORGANISM: Homo sapiens

<400> SEQUENCE: 13
aaatgtttgt gttgcggtca                                               20

<210> SEQ ID NO 14
<211> LENGTH: 20
<212> TYPE: DNA
<213> ORGANISM: Homo sapiens

<400> SEQUENCE: 14
tctggcacag gtgtcttcag                                               20

<210> SEQ ID NO 15
<211> LENGTH: 20
<212> TYPE: DNA
<213> ORGANISM: Homo sapiens

<400> SEQUENCE: 15
ctacgccaac atgaactcca                                               20

<210> SEQ ID NO 16
<211> LENGTH: 20
<212> TYPE: DNA
<213> ORGANISM: Homo sapiens

<400> SEQUENCE: 16
aaggggaaga ggtccatgat                                               20

<210> SEQ ID NO 17
<211> LENGTH: 19
<212> TYPE: DNA
<213> ORGANISM: Homo sapiens

<400> SEQUENCE: 17
cccatggatg aagtctacc                                                19

<210> SEQ ID NO 18
<211> LENGTH: 19
<212> TYPE: DNA
<213> ORGANISM: Homo sapiens

<400> SEQUENCE: 18
gtcctcctcc tttttccac                                                19
```

```
<210> SEQ ID NO 19
<211> LENGTH: 23
<212> TYPE: DNA
<213> ORGANISM: Homo sapiens

<400> SEQUENCE: 19
gtagaaagga tgacgcctca acc                                              23

<210> SEQ ID NO 20
<211> LENGTH: 22
<212> TYPE: DNA
<213> ORGANISM: Homo sapiens

<400> SEQUENCE: 20
tcagtgccaa ctcgctctta gg                                               22

<210> SEQ ID NO 21
<211> LENGTH: 22
<212> TYPE: DNA
<213> ORGANISM: Homo sapiens

<400> SEQUENCE: 21
atttccctat gtgttggttg cg                                               22

<210> SEQ ID NO 22
<211> LENGTH: 20
<212> TYPE: DNA
<213> ORGANISM: Homo sapiens

<400> SEQUENCE: 22
cgttcttgct gaagccgatg                                                  20

<210> SEQ ID NO 23
<211> LENGTH: 20
<212> TYPE: DNA
<213> ORGANISM: Homo sapiens

<400> SEQUENCE: 23
gaacgcagag gaggactcac                                                  20

<210> SEQ ID NO 24
<211> LENGTH: 20
<212> TYPE: DNA
<213> ORGANISM: Homo sapiens

<400> SEQUENCE: 24
gtggaagaca tgggagctgt                                                  20

<210> SEQ ID NO 25
<211> LENGTH: 21
<212> TYPE: DNA
<213> ORGANISM: Homo sapiens

<400> SEQUENCE: 25
acacgagacc cacttttttcc g                                               21

<210> SEQ ID NO 26
<211> LENGTH: 23
<212> TYPE: DNA
<213> ORGANISM: Homo sapiens

<400> SEQUENCE: 26
tgctggactt gtgcttcttc aac                                              23
```

<210> SEQ ID NO 27
<211> LENGTH: 20
<212> TYPE: DNA
<213> ORGANISM: Homo sapiens

<400> SEQUENCE: 27
gctaccgaca gcctattcta                                        20

<210> SEQ ID NO 28
<211> LENGTH: 20
<212> TYPE: DNA
<213> ORGANISM: Homo sapiens

<400> SEQUENCE: 28
caagtcccac tgacatgaag                                        20

<210> SEQ ID NO 29
<211> LENGTH: 22
<212> TYPE: DNA
<213> ORGANISM: Homo sapiens

<400> SEQUENCE: 29
cttcagcaag gaggaggtca tc                                     22

<210> SEQ ID NO 30
<211> LENGTH: 25
<212> TYPE: DNA
<213> ORGANISM: Homo sapiens

<400> SEQUENCE: 30
ctcgtatttc tccttgtaca ggtcc                                  25

<210> SEQ ID NO 31
<211> LENGTH: 20
<212> TYPE: DNA
<213> ORGANISM: Homo sapiens

<400> SEQUENCE: 31
agcctttgtg aaccaacacc                                        20

<210> SEQ ID NO 32
<211> LENGTH: 20
<212> TYPE: DNA
<213> ORGANISM: Homo sapiens

<400> SEQUENCE: 32
gctggtagag ggagcagatg                                        20

<210> SEQ ID NO 33
<211> LENGTH: 19
<212> TYPE: DNA
<213> ORGANISM: Homo sapiens

<400> SEQUENCE: 33
aggcagaccc actcagtga                                         19

<210> SEQ ID NO 34
<211> LENGTH: 20
<212> TYPE: DNA
<213> ORGANISM: Homo sapiens

<400> SEQUENCE: 34
aacaatggcg acctcttctg                                          20

<210> SEQ ID NO 35
<211> LENGTH: 22
<212> TYPE: DNA
<213> ORGANISM: Homo sapiens

<400> SEQUENCE: 35
gtacttcttg gcagagctgc tg                                       22

<210> SEQ ID NO 36
<211> LENGTH: 22
<212> TYPE: DNA
<213> ORGANISM: Homo sapiens

<400> SEQUENCE: 36
cagaagaaat tcttgcagcc ag                                       22

<210> SEQ ID NO 37
<211> LENGTH: 20
<212> TYPE: DNA
<213> ORGANISM: Homo sapiens

<400> SEQUENCE: 37
agccacatcg ctcagacacc                                          20

<210> SEQ ID NO 38
<211> LENGTH: 20
<212> TYPE: DNA
<213> ORGANISM: Homo sapiens

<400> SEQUENCE: 38
gtactcagcg gccagcatcg                                          20

<210> SEQ ID NO 39
<211> LENGTH: 29
<212> TYPE: DNA
<213> ORGANISM: Homo sapiens

<400> SEQUENCE: 39
cctagccatg cactactcac cagacgcct                                29

<210> SEQ ID NO 40
<211> LENGTH: 28
<212> TYPE: DNA
<213> ORGANISM: Homo sapiens

<400> SEQUENCE: 40
ctgtctactg agtagcctcc tcagattc                                 28

<210> SEQ ID NO 41
<211> LENGTH: 33
<212> TYPE: DNA
<213> ORGANISM: Homo sapiens

<400> SEQUENCE: 41
tcaccaaaga gcccctaaaa cccgccacat cta                           33

<210> SEQ ID NO 42
<211> LENGTH: 24
<212> TYPE: DNA
<213> ORGANISM: Homo sapiens

<400> SEQUENCE: 42

```
taagggtgga gaggttaaag gagc                                          24

<210> SEQ ID NO 43
<211> LENGTH: 20
<212> TYPE: DNA
<213> ORGANISM: Homo sapiens

<400> SEQUENCE: 43
tgtgcaccaa catctacaag                                               20

<210> SEQ ID NO 44
<211> LENGTH: 20
<212> TYPE: DNA
<213> ORGANISM: Homo sapiens

<400> SEQUENCE: 44
gcgttcttgg ctttcaggat                                               20

<210> SEQ ID NO 45
<211> LENGTH: 20
<212> TYPE: DNA
<213> ORGANISM: Homo sapiens

<400> SEQUENCE: 45
agcctttgtg aaccaacacc                                               20

<210> SEQ ID NO 46
<211> LENGTH: 20
<212> TYPE: DNA
<213> ORGANISM: Homo sapiens

<400> SEQUENCE: 46
gctggtagag ggagcagatg                                               20

<210> SEQ ID NO 47
<211> LENGTH: 22
<212> TYPE: DNA
<213> ORGANISM: Homo sapiens

<400> SEQUENCE: 47
gtacttcttg gcagagctgc tg                                            22

<210> SEQ ID NO 48
<211> LENGTH: 22
<212> TYPE: DNA
<213> ORGANISM: Homo sapiens

<400> SEQUENCE: 48
cagaagaaat tcttgcagcc ag                                            22

<210> SEQ ID NO 49
<211> LENGTH: 19
<212> TYPE: DNA
<213> ORGANISM: Homo sapiens

<400> SEQUENCE: 49
aggcagaccc actcagtga                                                19

<210> SEQ ID NO 50
<211> LENGTH: 20
<212> TYPE: DNA
<213> ORGANISM: Homo sapiens
```

```
<400> SEQUENCE: 50
aacaatggcg acctcttctg                                               20

<210> SEQ ID NO 51
<211> LENGTH: 20
<212> TYPE: DNA
<213> ORGANISM: Homo sapiens

<400> SEQUENCE: 51
gctaccgaca gcctattcta                                               20

<210> SEQ ID NO 52
<211> LENGTH: 20
<212> TYPE: DNA
<213> ORGANISM: Homo sapiens

<400> SEQUENCE: 52
caagtcccac tgacatgaag                                               20

<210> SEQ ID NO 53
<211> LENGTH: 21
<212> TYPE: DNA
<213> ORGANISM: Homo sapiens

<400> SEQUENCE: 53
aagaagtcca agctggagtt c                                             21

<210> SEQ ID NO 54
<211> LENGTH: 21
<212> TYPE: DNA
<213> ORGANISM: Homo sapiens

<400> SEQUENCE: 54
gttggtctgg aattctgtca g                                             21
```